US008044072B2

(12) United States Patent
Barth et al.

(10) Patent No.: US 8,044,072 B2
(45) Date of Patent: Oct. 25, 2011

(54) PYRROLE DERIVATIVES, PREPARATION THEREOF AND THERAPEUTIC USE THEREOF

(75) Inventors: Francis Barth, Saint Georges D'Orques (FR); Christian Congy, Saint Gely du Fesc (FR); Laurent Hortala, Montpellier (FR); Murielle Rinaldi-Carmona, Saint Georges D'Orques (FR)

(73) Assignee: Sanofi Aventis, Paris (FR)

( * ) Notice: Subject to any disclaimer, the term of this patent is extended or adjusted under 35 U.S.C. 154(b) by 253 days.

(21) Appl. No.: 12/465,893

(22) Filed: May 14, 2009

(65) Prior Publication Data
US 2009/0281116 A1 Nov. 12, 2009

Related U.S. Application Data

(63) Continuation of application No. PCT/FR2007/001888, filed on Nov. 19, 2007.

(30) Foreign Application Priority Data
Nov. 20, 2006 (FR) ..................................... 06 10202

(51) Int. Cl.
*A61K 31/454* (2006.01)
*A61K 31/4439* (2006.01)
*A61K 31/40* (2006.01)
*C07D 401/02* (2006.01)
*C07D 401/14* (2006.01)

(52) U.S. Cl. ........ 514/326; 514/343; 514/427; 546/187; 546/268.1; 548/531; 548/537

(58) Field of Classification Search .................. 546/187, 546/268.1; 548/531, 537; 514/326, 343, 514/427
See application file for complete search history.

(56) References Cited

FOREIGN PATENT DOCUMENTS
WO  WO 03/007887    1/2003
WO  WO 2006/024777  3/2006

OTHER PUBLICATIONS

Bouaboula, M., et. al., A Selective Inverse Agonist for Central Cannabinoid Receptor Inhibits Mitogen-Activated Protein Kinase Activation Stimulated by Insulin or Insulin-Like Growth Factor 1, The Journal of Biological Chemistry, vol. 272, No. 35, (1997), pp. 22330-22339.
Bouaboula, et. al., Stimulation of Cannabinoid Receptor CB1 Induces Krox-24 Expression in Human Astrocytoma Cells, The Journal of Biological Chemistry, vol. 270, No. 23, (1995), pp. 13973-13980.
Knight, D. W., et. al., An Approach to 2,3-Dihydropyrroles and B-Iodopyrroles Based on 5-Endo-Dig Cyclisations, J. Chem. Soc., Perkin Trans., vol. 1, pp. 622-628, (2002).
Rinaldi-Carmona, M., et. al., Biochemical and Pharmacological Characterisation of SR141716A, The First Potent and Selective Brain Cannabinoid Receptor Antagonist, Life Sciences, vol. 56, No. 23/24, pp. 1941-1947, (1995).
Rinaldi-Carmona, M., et. al., Characterization of Two Cloned Human CB1 Cannabinoid Receptor Isoforms, The Journal of Pharmacology and Experimental Therapeutics, vol. 278, No. 2, pp. 871-878, (1996).
Rinaldi-Carmona, M., et. al., SR141716A, A Potent and Selective Antogonist of the Brain Cannabinoid Receptor, Febs Letters, vol. 350, (1994) pp. 240-244.
Rinaldi-Carmona, M., et. al., SR147778 [5-(4-Bromophenyl)-1-(2,4-Dichlorophenyl)-4-ethyl-N-(1-Piperidinyl)-1H-Pyrazole-3-Carboxamide], A New Potent and Selective Antagonist of the CB1 Cannabinoid Receptor: Biochemical and Pharmacological Characterization, The Journal of Pharmacology and Experimental Therapeutics, vol. 310, No. 3, (2004), pp. 905-914.
Westeringh, C., et. al., 4-Substituted Piperidines. I. Derivatives of 4-T-Amino-4-Piperidinecarboxamides, Journal of Medicinal Chemistry, (1964), vol. 7, No. 5, 619-623.

*Primary Examiner* — Rebecca Anderson
*Assistant Examiner* — Samantha Shterengarts
(74) *Attorney, Agent, or Firm* — Scully, Scott, Murphy & Presser, P.C.

(57) ABSTRACT

The invention relates to compounds having the formula (I):

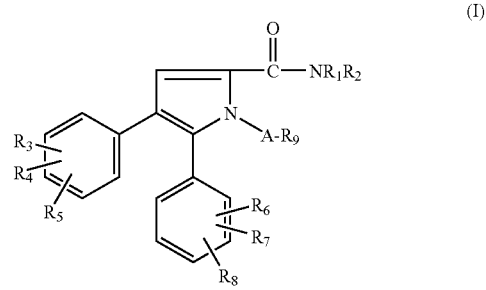

Wherein $R_1$, $R_2$, $R_3$, $R_4$, $R_5$, $R_6$, $R_7$ and $R_8$ and A-$R_9$ are as defined herein. Also disclosed are the preparative methods for the compounds of formula (I) and their use in therapy.

10 Claims, No Drawings

PYRROLE DERIVATIVES, PREPARATION THEREOF AND THERAPEUTIC USE THEREOF

CROSS REFERENCE TO RELATED APPLICATIONS

This application is a continuation of International application No. PCT/FR2007/001,888, filed Nov. 19, 2007, which is incorporated herein by reference in its entirety; which claims the benefit of priority of French Patent Application No. 06/10,202, filed Nov. 20, 2006.

BACKGROUND OF THE INVENTION

1. Field of the Invention

The present invention relates to 4,5-diphenylpyrrole-2-carboxamide derivatives, to their preparation and to their therapeutic application.

2. Description of the Art 4,5-Diphenylpyrrole-2-carboxamide derivatives with affinity for the cannabinoid $CB_1$ receptors have been described in patent application WO 2006/024 777.

Novel 4,5-diphenylpyrrole-2-carboxamide derivatives bearing a particular substituent on the pyrrole nitrogen have now been found, which have antagonist properties on the central and/or peripheral cannabinoid $CB_1$ receptors.

SUMMARY OF THE INVENTION

The present invention relates to compounds corresponding to the formula:

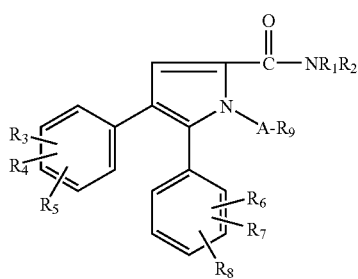

(I)

in which:

A represents:
  a $(C_1-C_6)$alkylene group, which is unsubstituted or substituted one or more times with a $(C_1-C_3)$alkyl group;
  a group

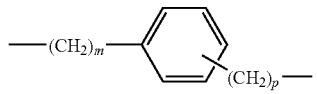

with m=0, 1 or 2 and p=0 or 1;

$R_1$ represents hydrogen or a $(C_1-C_4)$alkyl;

$R_2$ represents:
  a $(C_3-C_{10})$alkyl group, which is unsubstituted or substituted with a trifluoromethyl group; hydroxyl, $(C_1-C_4)$alkoxy, a fluorine atom or a $CONH_2$ group;
  a non-aromatic $C_3-C_{12}$ carbocyclic radical, which is unsubstituted or substituted one or more times with a $(C_1-C_4)$alkyl, hydroxyl, cyano or $(C_1-C_4)$alkoxy group, a group $COR_{12}$ or a fluorine atom;
  an indanyl;
  a 1,2,3,4-tetrahydro-1- or -2-naphthyl;
  a monooxygen or monosulfur heterocyclic radical of 5 to 7 atoms, which is unsubstituted or substituted one or more times with a $(C_1-C_4)$alkyl group;
  a mononitrogen heterocyclic radical of 5 to 7 atoms, which is unsubstituted or substituted one or more times with a $(C_1-C_4)$alkyl group, the nitrogen atom moreover being substituted with a $(C_1-C_4)$alkyl, phenyl, benzyl, $(C_1-C_4)$alkoxycarbonyl or $(C_1-C_4)$alkanoyl group, the phenyl or benzyl groups being unsubstituted or substituted one or more times with a halogen atom or a $(C_1-C_4)$alkyl, trifluoromethyl, hydroxyl or $(C_1-C_4)$alkoxy group;
  a benzothiophenyl or an indolyl, the said radicals being unsubstituted or substituted one or more times with a $(C_1-C_4)$alkyl group;
  a $(C_1-C_3)$alkylene group bearing a non-aromatic $C_3-C_{10}$ carbocyclic radical, which is unsubstituted or substituted one or more times with a $(C_1-C_4)$alkyl, hydroxyl, $(C_1-C_4)$alkoxy or cyano group or a group $COR_{12}$;
  a $(C_1-C_3)$alkylene group bearing a monooxygen, monosulfur or mononitrogen heteroaromatic or non-heteroaromatic heterocyclic radical of 5 to 7 atoms, which is unsubstituted or substituted one or more times with a $(C_1-C_4)$alkyl group;
  a $(C_1-C_3)$alkylene group bearing an indolyl or benzothiophenyl radical, the said radical being unsubstituted or substituted one or more times with a $(C_1-C_4)$alkyl group and the alkylene being unsubstituted or substituted with a hydroxyl, methyl or methoxy group or with a group $COR_{12}$;
  a $(C_1-C_3)$alkylene group bearing a $(C_1-C_4)$alkylthio group;
  a phenylalkylene group in which the alkylene is $(C_1-C_3)$, which is unsubstituted or substituted on the alkylene with one or more methyl, hydroxyl, hydroxymethyl, methoxy or methoxymethyl groups, or a group $COR_{12}$, and which is unsubstituted on the phenyl or substituted on the phenyl with one or more identical or different substituents chosen from a halogen atom and a $(C_1-C_4)$alkyl, trifluoromethyl, $(C_1-C_4)$alkoxy or trifluoromethoxy group;
  a benzhydryl or benzhydrylmethyl group;
  a group $NR_{10}R_{11}$;

or $R_1$ and $R_2$, together with the nitrogen atom to which they are attached, constitute:
  either a morpholinyl group
  or a piperazin-1-yl or 1,4-diazepan-1-yl radical, which is unsubstituted or substituted with a phenyl, benzyl, benzodioxolyl, benzodioxolylmethyl or tetrahydrofurylcarbonyl group or with a group $COR_{12}$ or $CH_2COR_{12}$, the benzyl group itself being unsubstituted or substituted with one or more halogen atoms or with one or more methoxy or methoxymethyl groups;
  or a piperid-1-yl, pyrrolidin-1-yl or azetidin-1-yl radical, which is unsubstituted or substituted one or two times with a substituent independently chosen from:
    a fluorine atom or a group $(C_1-C_4)$alkyl, hydroxyl, cyano, $COR_{12}$, $NR_{13}R_{14}$, $NHCOR_{15}$, $CH_2COR_{12}$, $SO_2Alk$; or $SO_2NR_{13}R_{14}$;
    a phenyl, benzyl or pyridyl group, the said phenyl, benzyl or pyridyl groups being unsubstituted or substituted one or more times with a substituent each independently chosen from a halogen atom, and a methyl, trifluoromethyl, hydroxyl, $(C_1-C_4)$ alkoxy or cyano group;

a piperid-1-yl, pyrrolidin-1-yl or azetidin-1-yl group, the said piperid-1-yl, pyrrolidin-1-yl or azetidin-1-yl groups being unsubstituted or substituted one or more times with a fluorine atom or a $(C_1-C_4)$alkyl, $(C_1-C_4)$alkoxy, hydroxyl, trifluoromethyl or $OCF_3$ group;

$R_3$, $R_4$, $R_5$, $R_6$, $R_7$ and $R_8$ represent, independently of each other, a hydrogen or halogen atom, a group CN, $S(O)_n$ALK or $OS(O)_n$ALK, a group $(C_1-C_7)$alkyl, which is unsubstituted or substituted one or more times with a substituent each independently chosen from a fluorine atom, and group OALK, $S(O)_n$ALK, $OS(O)_n$ALK and $NHSO_2$Alk, or a group $(C_1-C_6)$alkoxy, which is unsubstituted or substituted with one or more substituents each independently chosen from a fluorine atom and a group OALK, $S(O)_n$ALK, $OS(O)_n$ALK and $NHSO_2$Alk;

$R_9$ represents a group —OH, —CN, —$CO_2H$, $NR_{13}R_{14}$, —$CONR_{13}R_{14}$, $NR_1COR_{13}$, —$CONHNH_2$, —CONHOH, —$CONHSO_2$Alk, —$S(O)_n$Alk, —$SO_2CF_3$, —$SO_2NR_{13}R_{14}$, —$NR_1SO_2$Alk, —$NR_1SO_2CF_3$, —$NR_1SO_2NR_{13}R_{14}$, or a radical chosen from:

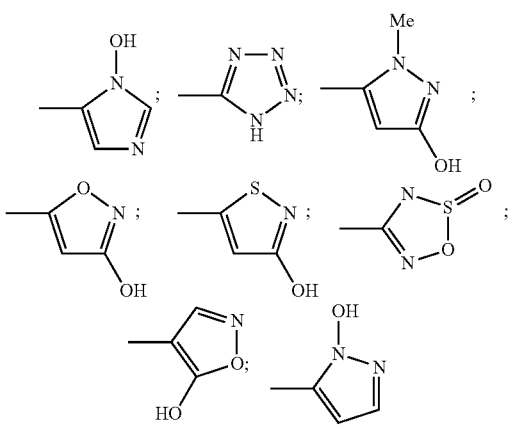

$R_{10}$ represents a hydrogen atom or a methyl group;
$R_{11}$ represents a $(C_3-C_6)$alkyl, phenyl or $(C_3-C_{10})$cycloalkyl group, the said phenyl and cycloalkyl groups being unsubstituted or substituted with one or more substituents independently chosen from a halogen atom and a $(C_1-C_4)$alkyl or trifluoromethyl group;
or $R_{10}$ and $R_{11}$, together with the nitrogen atom to which they are attached, constitute a saturated or unsaturated, bridged or non-bridged heterocyclic radical of 4 to 11 atoms, possibly comprising a spirane carbon and possibly containing a second heteroatom chosen from O and N, the said radical being unsubstituted or substituted one or more times with a substituent each independently chosen from a hydroxyl, $(C_1-C_4)$alkyl or $(C_1-C_4)$alkoxycarbonyl or $COR_{12}$ group, or a phenyl group that is unsubstituted or substituted with one or more substituents independently chosen from a halogen atom and a $(C_1-C_4)$alkyl group;
$R_{12}$ represents a $(C_1-C_4)$alkyl, phenyl, benzyl, $(C_1-C_4)$ alkoxy or trifluoromethyl group or a group $NR_{13}R_{14}$;
$R_{13}$ and $R_{14}$ each independently represent a hydrogen atom or a $(C_1-C_6)$alkyl group optionally substituted with one or more groups OH, F or OALK, or $R_{13}$ or $R_{14}$, together with the nitrogen atom to which they are attached, constitute a 4- to 7-membered heterocyclic radical possibly comprising a second heteroatom chosen from a nitrogen, oxygen or sulfur atom;
$R_{15}$ represents a $(C_1-C_4)$alkyl or trifluoromethyl group;
n represents 0, 1 or 2;
ALK represents a $(C_1-C_4)$alkyl group, which is unsubstituted or substituted with one or more fluorine atoms;
Alk represents a $(C_1-C_4)$alkyl group;
and also the salts, solvates and hydrates thereof.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or of acid-addition salts. These salts are advantageously prepared with pharmaceutically acceptable acids, but the salts of other acids that are useful, for example, for purifying or isolating the compounds of formula (I) also form part of the invention.

The compounds according to the invention may also exist in the form of hydrates or solvates, i.e. in the form of associations or combinations with one or more water molecules or with a solvent. Such hydrates and solvates also form part of the invention.

DETAILED DESCRIPTION OF THE INVENTION

The term "alkyl group" means a linear or branched radical such as, in particular: methyl, ethyl, propyl, isopropyl, butyl, isobutyl, tert-butyl, n-pentyl, isopentyl, n-hexyl, isohexyl, the methyl group being preferred for a $(C_1-C_4)$alkyl, and the tert-butyl, 2-methyl-2-butyl and 3,3-dimethyl-2-butyl groups being preferred for a $(C_4-C_{10})$alkyl.

The term "alkylene group" means a linear divalent radical.
The term "alkoxy group" means a linear or branched radical, the methoxy group being preferred.
The term "halogen atom" means a fluorine, chlorine, bromine or iodine atom; fluorine, chlorine or bromine atoms being preferred.

The non-aromatic $C_3-C_{12}$ carbocyclic radicals comprise bridged or fused monocyclic or polycyclic radicals. The monocyclic radicals include cycloalkyls, for example cyclopropyl, cyclobutyl, cyclopentyl, cyclohexyl, cycloheptyl and cyclooctyl; cyclohexyl and cyclopentyl being preferred. The fused, bridged or spirane bicyclic or tricyclic radicals include, for example, norbornyl, bornyl, isobornyl, noradamantyl, adamantyl, spiro[5.5]undecanyl, bicyclo[2.2.1]heptanyl, bicyclo[3.2.1]octanyl and bicyclo[3.1.1]heptanyl radicals.

The term "saturated or unsaturated heterocyclic radical of 4 to 11 atoms, possibly containing a second heteroatom such as O or N" means radicals such as morpholin-4-yl, piperid-1-yl, piperazin-1-yl, pyrrolidin-1-yl or octahydrocyclopenta[c]pyrrol-2-yl, the piperid-1-yl and morpholin-4-yl radicals being preferred.

The term "mononitrogen heterocyclic radical of 5 to 7 atoms" means a radical such as piperid-4-yl or pyrrolidin-3-yl, the piperid-4-yl radical being preferred.

The term "monooxygen heterocyclic radical of 5 to 7 atoms" means a radical such as tetrahydrofuryl, tetrahydro-2H-pyranyl or oxepanyl; tetrahydrofuryl being preferred.

The term "monosulfur heterocyclic radical of 5 to 7 atoms" means a radical such as tetrahydrothiophenyl or tetrahydrothiopyranyl.

The term "heteroaromatic heterocyclic radical of 5 to 7 atoms" means a radical such as pyridyl, pyrrolyl, thiophenyl or furanyl.

The expression "5- to 7-membered nitrogenous heterocyclic radical possibly comprising a second heteroatom chosen from a nitrogen, oxygen or sulfur atom" in particular means an azetidinyl, pyrrolidinyl, piperazinyl, piperidyl, azepinyl, morpholinyl, thiomorpholinyl or piperazinyl radical.

According to the present invention, the following are distinguished:
the compounds of formula IA in which -A- represents a ($C_1$-$C_6$)alkylene group, which is unsubstituted or substituted one or more times with a ($C_1$-$C_3$)alkylene;
the compounds of formula IB in which -A- represents a phenylene;
the compounds of formula IC in which -A- represents a group

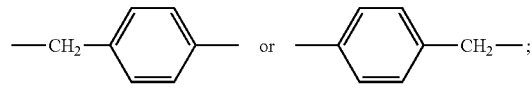

the compounds of formula ID in which -A- represents a group

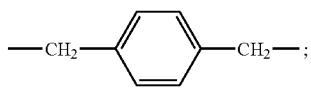

the compounds of formula IE in which -A- represents a group

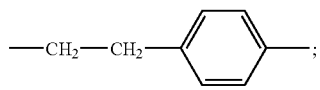

the compounds of formula IF in which -A- represents a group

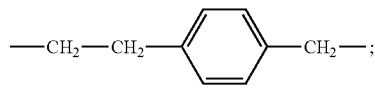

the substituents $R_1$ to $R_9$ being as defined for the compounds of formula (I).

According to the present invention, the compounds of formula (I) that are preferred are those in which:
$R_1$ represents hydrogen and $R_2$ represents a group $NR_{10}R_{11}$ in which $R_{10}$ and $R_{11}$, together with the nitrogen atom to which they are attached, constitute a saturated heterocyclic radical of 5 to 11 carbon atoms, which is unsubstituted or substituted one or more times with a ($C_1$-$C_4$) alkyl;
or $R_1$ and $R_2$, together with the nitrogen atom to which they are attached, constitute a piperid-1-yl radical substituted with a phenyl, benzyl, pyrrolidin-1-yl, piperid-1-yl or 4,4-difluoropiperid-1-yl group and with a cyano, ($C_1$-$C_3$)alkanoyl, aminocarbonyl, methanesulfonyl, N-methylsulfonyl or N,N-dimethylsulfonyl group;
or $R_1$ and $R_2$ together represent a piperazin-1-yl group 4-substituted with a benzodioxolyl or benzodioxolylmethyl group or with a benzyl group, which is itself unsubstituted or substituted with one or more halogen atoms or with one or more methoxy or methoxymethyl groups;
and/or $R_3$, $R_4$, $R_5$, $R_6$, $R_7$ and $R_8$ represent, independently of each other, a hydrogen or halogen atom or a methoxy group;
A-$R_9$ has one of the values indicated for (1);
and also the salts, solvates and hydrates thereof.

The compounds of formula I that are distinguished in particular are those in which;
$R_1$ represents hydrogen and $R_2$ represents a piperid-1-yl radical or a ($C_1$-$C_3$)alkylene radical substituted with a phenyl and with a methoxy or methoxycarbonyl group;
or $R_1$ represents hydrogen and $R_2$ represents a phenylalkylene group in which the alkylene is of ($C_1$-$C_3$), unsubstituted on the alkylene or substituted on the alkylene with a methyl, hydroxyl, hydroxymethyl, methoxy or methoxymethyl group, and unsubstituted on the phenyl or substituted one or more times on the phenyl with a halogen atom or a methyl, trifluoromethyl, hydroxyl or methoxy group;
or $R_1$ and $R_2$, together with the nitrogen atom to which they are attached, represent a piperid-1-yl radical 4-gem-disubstituted with a phenyl or piperid-1-yl group and with an acetyl, aminocarbonyl or cyano group;
or $R_1$ and $R_2$ together represent a piperazin-1-yl group 4-substituted with a benzodioxolylmethyl or a benzyl, which is itself unsubstituted or substituted with a halogen atom;
$R_6$ is a 4-chloro or a 4-methoxy and $R_3$ and $R_4$ represent 2,4-dichloro or 2-chloro, $R_5$, $R_7$ and $R_8$ representing a hydrogen atom;
A represents a group $(CH_2)_q$ with q=2, 3, 4 or 5;
$R_9$ represents a group chosen from: —$CO_2H$, —$NHSO_2CF_3$, —$NHSO_2CH_3$, —$SO_2CH_3$;
and also the salts, solvates and hydrates thereof.

In particular, the compounds of formula (I) that are preferred are those in which:
$NR_1R_2$ represents:

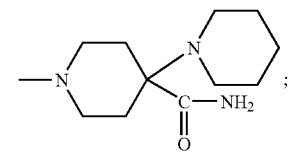

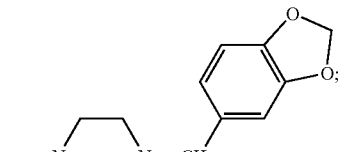

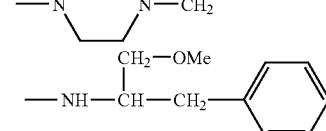

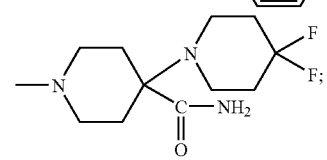

-continued

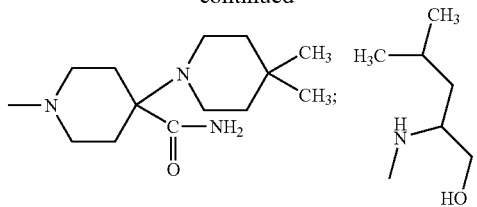

$R_3$, $R_4$ and $R_6$ each represent a halogen atom;
$R_5$, $R_7$ and $R_8$ each represent a hydrogen atom;
A represents a benzyl or a ($C_2$-$C_5$)alkylene group, which is unsubstituted or substituted one or more times with a methyl;
$R_9$ represents a group CN, $CO_2H$, $SO_2CH_3$, $NHSO_2CH_3$ or $NHSO_2CF_3$;
and also the salts thereof, solvates thereof and hydrates thereof.

The compounds of formula (I) that are distinguished are those in which:
$NR_1R_2$ represents a group chosen from:

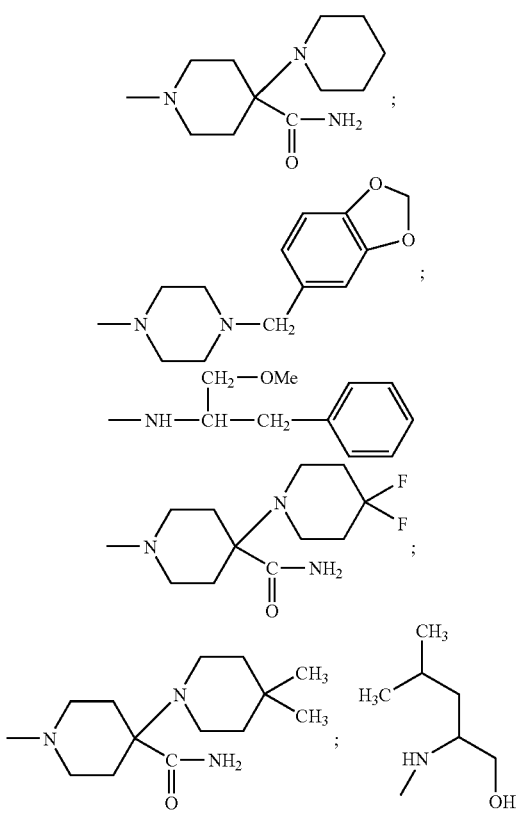

$R_3$, $R_4$ and $R_6$ each represent a halogen atom;
$R_5$, $R_7$ and $R_8$ each represent a hydrogen atom;
A-$R_9$ represents a group chosen from: —$(CH_2)_5$—$CO_2$, —$(CH_2)_3$—$NHSO_2CF_3$, —$(CH_2)_3NHSO_2CH_3$, —$(CH_2)_3$—$SO_2Me$;
and also the salts thereof, solvates thereof and hydrates thereof.

Among the compounds according to the invention, mention may be made especially of the following compounds:
6-[5-(4'-carbamoyl-[1,4']bipiperid-1-ylcarbonyl)-2-(4-chlorophenyl)-3-(2,4-dichlorophenyl)-1H-pyrrol-1-yl]hexanoic acid;
1-({5-(4-bromophenyl)-4-(2,4-dichlorophenyl)-1-[2-(methylsulfonyl)ethyl]-1H-pyrrol-2-yl}carbonyl)-4-phenylpiperidine-4-carboxamide;
1-(1,3-benzodioxol-5-yl-methyl)-4-({5-(4-bromophenyl)-4-(2,4-dichlorophenyl)-1-[2-(methylsulfonyl)ethyl]-1H-pyrrol-2-yl}carbonyl)piperazine;
N-(1-benzyl-2-methoxyethyl)-5-(4-bromophenyl)-4-(2,4-dichlorophenyl)-1-[2-(methylsulfonyl)ethyl]-1H-pyrrole-2-carboxamide;
1'-{[5-(4-chlorophenyl)-4-(2,4-dichlorophenyl)-1-{3-[(methylsulfonyl)amino]-propyl}-1H-pyrrol-2-yl]carbonyl}-1,4'-bipiperidine-4'-carboxamide;
1'-{[5-(4-chlorophenyl)-4-(2,4-dichlorophenyl)-1-{3-[(trifluoromethylsulfonyl)amino]propyl}-1H-pyrrol-2-yl]carbonyl}-1,4'-bipiperidine-4'-carboxamide;
1'-[5-(4-chlorophenyl)-4-(2,4-dichlorophenyl)-1-(3-methanesulfonylaminopropyl)-1H-pyrrole-2-carbonyl]-4,4-difluoro[1,4']bipiperidinyl-4'-carboxamide;
1'-[5-(4-chlorophenyl)-4-(2,4-dichlorophenyl)-1-(3-methanesulfonylaminopropyl)-1H-pyrrole-2-carbonyl]-4,4-dimethyl[1,4']bipiperidinyl-4'-carboxamide;
5-(4-chlorophenyl)-4-(2,4-dichlorophenyl)-1-(3-methanesulfonylaminopropyl)-1H-pyrrole-((S)-1-hydroxymethyl-3-methylbutyl)-2-carboxamide;
1'-[5-(4-chlorophenyl)-4-(2,4-dichlorophenyl)-1-(3-methanesulfonylpropyl)-1H-pyrrole-2-carbonyl]-4,4-dimethyl-[1,4']bipiperidyl-4'-carboxamide;
the other compounds given in Table 1;
and also the salts thereof, solvates thereof and hydrates thereof.

A subject of the present invention is also a process for preparing the compounds according to the invention.

This process is characterized in that:
the acid of formula (II) or a functional derivative of this acid of formula:

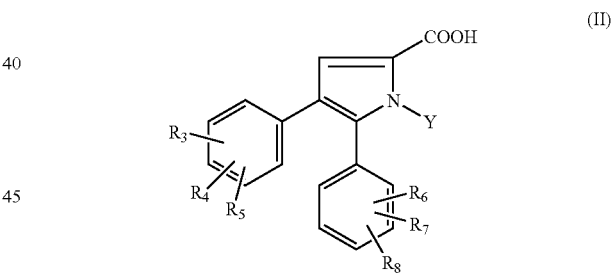

in which $R_3$, $R_4$, $R_5$, $R_6$, $R_7$ and $R_8$ are as defined for (I) and Y represents either a hydrogen atom or the group A-$R_9$, or a precursor of the group A-$R_9$, is treated with an amine of formula $HNR_1R_2$ (III) in which $R_1$ and $R_2$ are as defined for (I);
where appropriate, the substituent Y is converted into a group A-$R_9$.

Optionally, the compound thus obtained is converted into a salt or solvate thereof.

The term "precursor of the group A-$R_9$" means a group that may be subsequently converted into a group A-$R_9$ using methods known to those skilled in the art.

Functional derivatives of the acid (II) that may be used include the acid chloride, the anhydride, a mixed anhydride, a ($C_1$-$C_4$)alkyl ester in which the alkyl is straight or branched, a benzyl ester, an activated ester, for example the p-nitrophenyl ester, or the suitably activated free acid, for example activated with N,N-dicyclohexylcarbodiimide or with benzotriazol-1-yloxotris(dimethylamino)phosphonium hexafluorophosphate (BOP), benzotriazol-1-yloxotris(pyrrolidino)phosphonium hexafluorophosphate (PyBOP) or N-[1-N-(dimethylamino)-1,2,3-triazolo[4,5-b]pyrid-1-yl-methylene]-N-methylmethanaminium hexafluorophosphate N-oxide (HBTU).

Thus, in the process according to the invention, the 1,3-oxazole-3-carboxylic acid chloride, obtained by reacting thionyl chloride with the acid of formula (II), may be reacted with an amine $HNR_1R_2$, in an inert solvent, such as a chlorinated solvent (for example dichloromethane, dichloroethane or chloroform), an ether (for example tetrahydrofuran or dioxane) or an amide (for example N,N-dimethylformamide) under an inert atmosphere, at a temperature of between 0° C. and the room temperature, in the presence of a tertiary amine such as triethylamine, N-methylmorpholine or pyridine.

One variant consists in preparing the mixed anhydride of the acid of formula (II) by reacting ethyl chloroformate with the acid of formula (II), in the presence of a base such as triethylamine, and in reacting it with an amine $HNR_1R_2$, in a solvent such as dichloromethane, under an inert atmosphere, at room temperature, in the presence of a base such as triethylamine.

According to one variant, a compound of formula (I) in which one of the substituents $R_3$ to $R_8$ represents a hydroxyphenyl may be prepared by reacting a compound of formula (I) in which the substituent represents a methoxyphenyl with $BBr_3$, in a solvent such as dichloromethane and at a temperature of between −20° C. and room temperature.

According to another variant, a compound of formula (I) in which one of the substituents $R_3$ to $R_8$ represents an $AlkS(O)_n$ O-phenyl may be prepared by reacting a compound of formula (I) in which this substituent represents a hydroxyphenyl with a halide of formula $Hal-S(O)_nAlk$, in which Hal represents a halogen atom, preferably chlorine, in the presence of a base such as triethylamine, in a solvent such as dichloromethane and at a temperature of between −20° C. and room temperature.

The compounds of formula (I) thus obtained may subsequently be separated from the reaction medium and purified according to standard methods, for example by crystallization or chromatography.

The compounds of formula (II) and the precursors thereof may be prepared according to the following scheme:

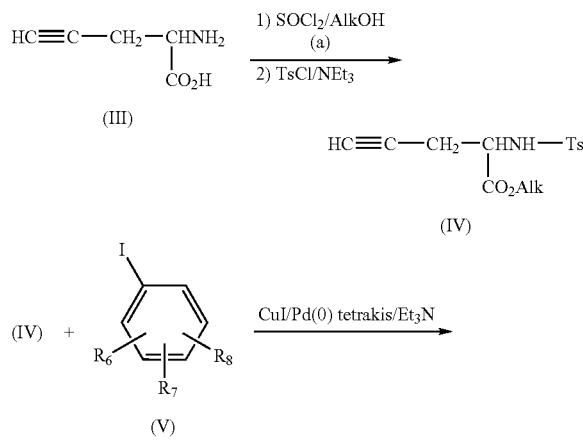

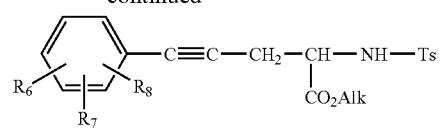

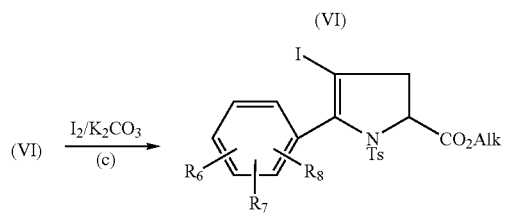

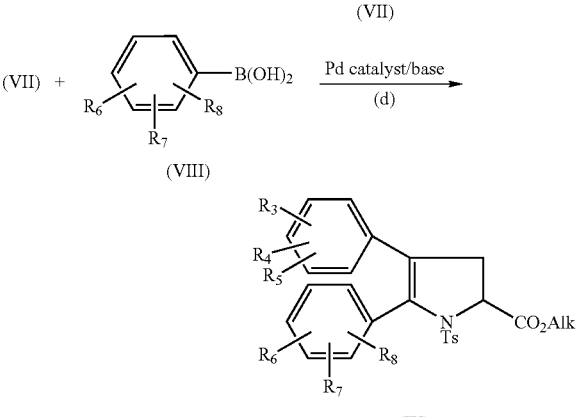

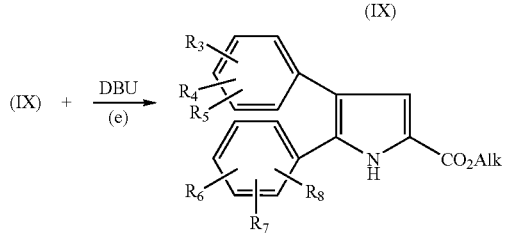

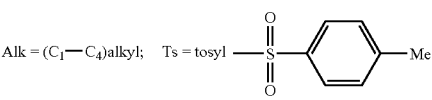

The preparation of the dihydropyrrole derivative of formula (VII) via steps a), b) and c) is performed according to J. Chem. Soc. Perkin Trans. 1, 2002, 622-628.

The substitution of the dihydropyrrole nucleus with a substituted phenyl group is performed in step d) via the action of a substituted phenylboronic acid of formula (VIII) in the presence of a palladium catalyst such as tetrakis(triphenylphosphine)Pd(0), bisdibenzylideneacetonepalladium(0) [Pd(dba)$_2$], tris(dibenzylideneacetone)dipalladium(0), palladium acetate Pd(II)[Pd(OCOCH$_3$)$_2$], dichloro(diphenylphosphinoferrocene)Pd(II) [PdCl$_2$dppf], and in the presence of a base.

In step e) the tosyl protecting group on the nitrogen is removed via the action of a diamine such as DBU (1,8-diazabicyclo[5.4.0]undecene), and the pyrrole nucleus is simultaneously aromatized.

According to one general process, the compound of formula (X) is then treated with an iodide of formula $R_9$-A-I to give a compound of formula:

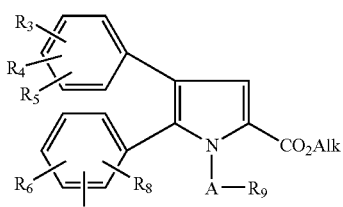

(XI) = Ester of the acid acid of formula (II)

The ester of formula (XI) is then hydrolyzed in basic medium and the acid (II) thus formed is treated with the amine $HNR_1R_2$ (III) to form compound (I) according to the invention.

Depending on the various values of the group -A-$R_9$, various methods known to those skilled in the art may be used to prepare the compounds of formula (II) and the compounds of formula (I) according to the invention.

Thus, when a compound of formula (I) in which -A-$R_9$ represents the group $(CH_2)_3NHSO_2Alk$ is prepared, the process may be performed according to Scheme 2 below:

SCHEME 2

(X) + acrylonitrile ⟶

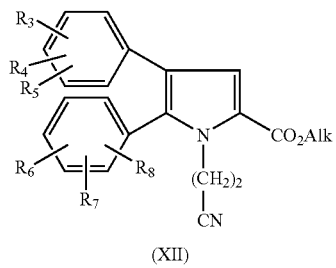

(XII)

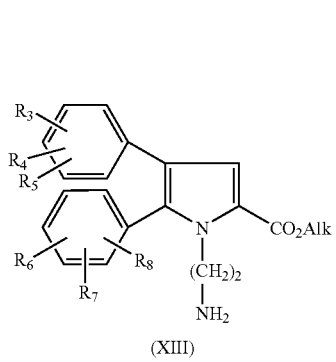

(XIII)

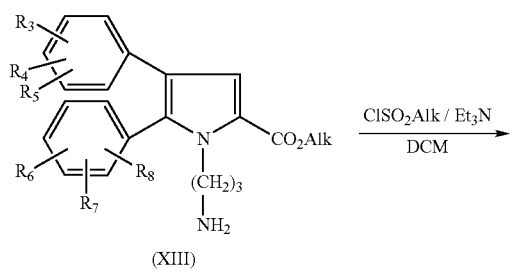

(XIII)

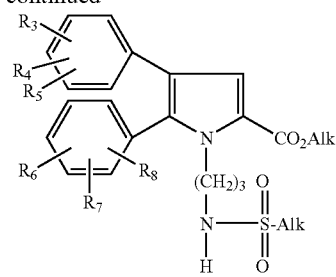

(XIV)

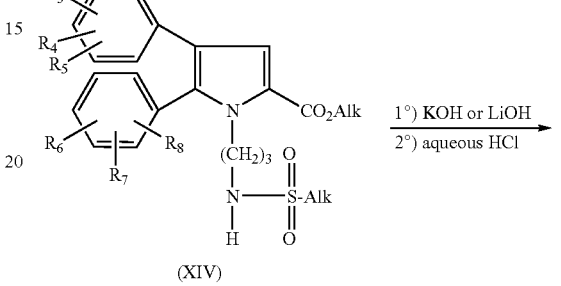

(XIV)

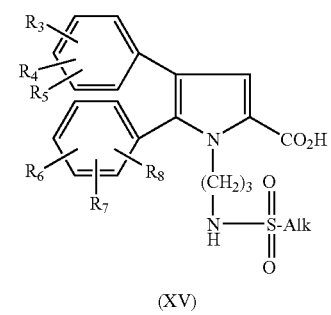

(XV)

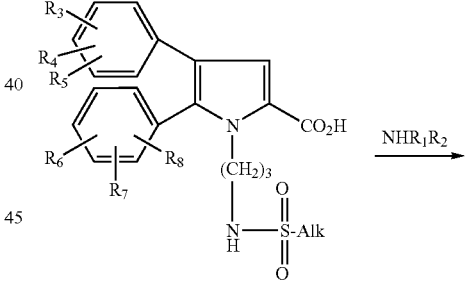

(XV)

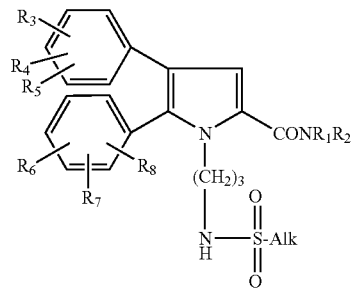

(I, A-$R_9$ = $(CH_2)_3NHSO_2Alk$)

A compound of formula (I) in which A-$R_9$ represents a group —$(CH_2)_2NHCOR_{13}$ is prepared from compound (XIII) and $R_{13}CO_2H$ in the presence of a coupling agent (e.g. HBTU, BOP, PyBOP) and a base (e.g. $N(Et)_3$).

When a compound of formula (I) is prepared in which A-$R_9$ represents a group —$(CH_2)_2SO_2Alk$, the process may be performed according to Scheme 3 below:

SCHEME 3

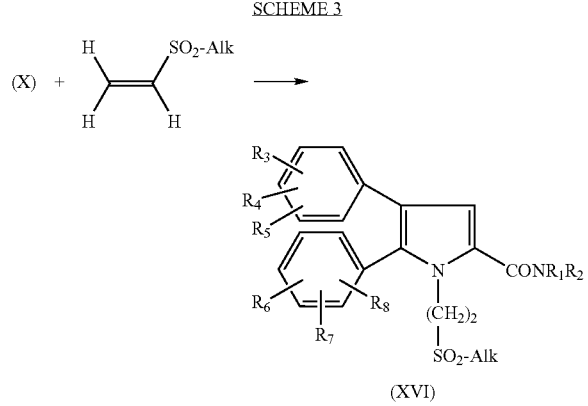

When a compound of formula (I) is prepared in which A-$R_9$ represents a group —$(CHZ)_kSO_2Alk$ with k=1, 2, 3, 4, 5 or 6, the process may be performed according to Scheme 4 below:

SCHEME 4

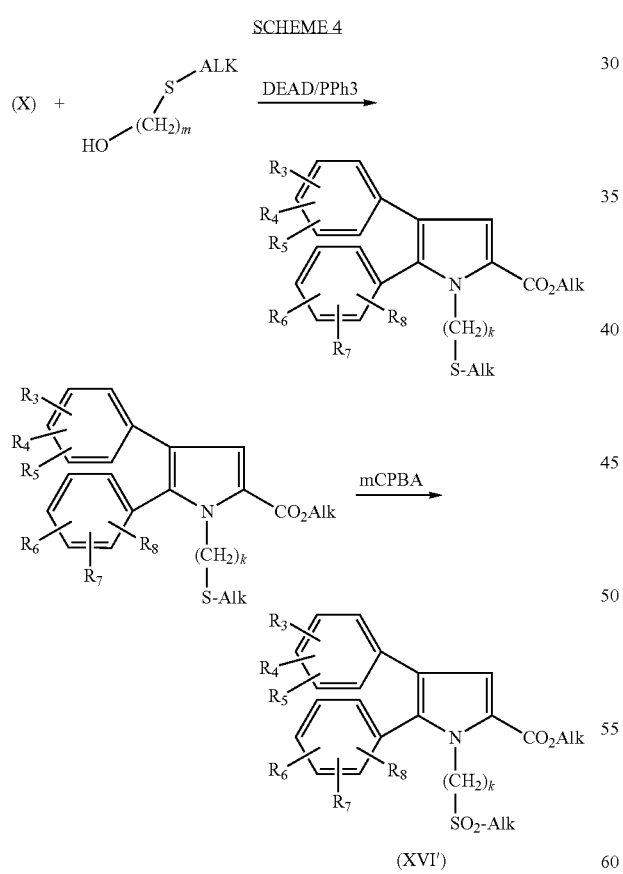

Starting with the compound of formula (XVI) or of formula (XVI'), the process is performed as in reaction scheme 2 by saponification followed by coupling with the compound of formula $NR_1R_2$ to give the compound of formula (I) in which A-$R_9$=$(CH_2)_2$-Alk or A-$R_9$=$(CH_2)_k$-Alk.

When a compound of formula (I) is prepared, in which $R_9$ represents a —COOH group, the process may be performed according to Scheme 5 below:

SCHEME 5

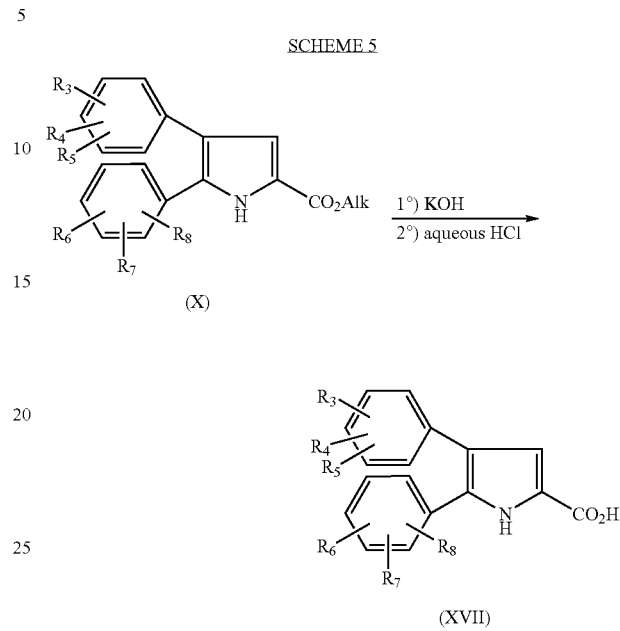

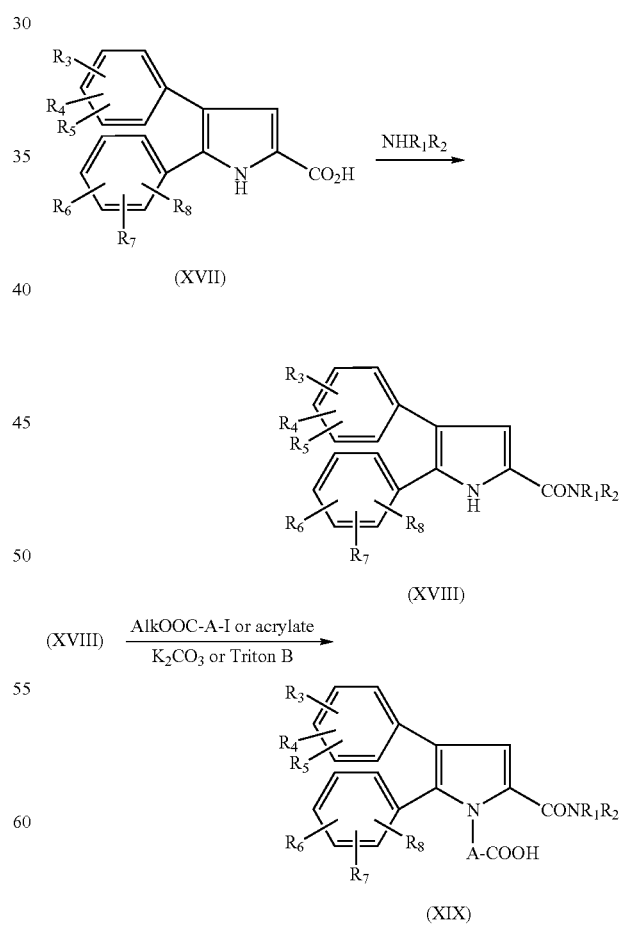

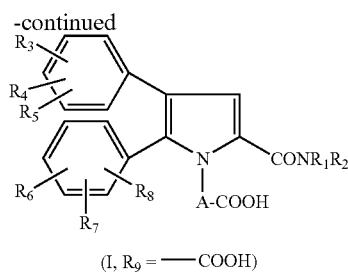

(I, R$_9$ = ——COOH)

The amines of formula IINR$_1$R$_2$ (III) are known or prepared via known methods, for example those described in J. Med. Chem., 7, 1964, 619-622.

A subject of the present invention is also the compounds of formula:

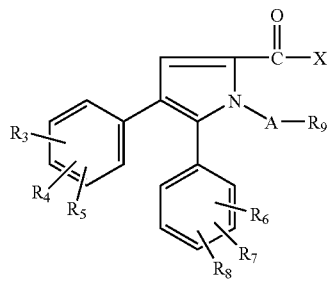

(II bis)

in which:

X represents a halogen atom or a hydroxyl, (C$_1$-C$_4$)alkoxy or benzyloxy group;

A represents:
  a (C$_1$-C$_6$)alkylene group, which is unsubstituted or substituted one or more times with a (C$_1$-C$_3$)alkyl group;
  a group

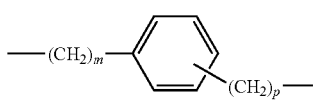

with m=0, 1 or 2 and p=0 or 1;

R$_3$, R$_4$, R$_5$, R$_6$, R$_7$ and R$_8$ represent, independently of each other, a hydrogen or halogen atom, a (C$_1$-C$_6$)alkoxy group, a group S(O)$_n$ALK, OS(O)$_n$ALK or a (C$_1$-C$_7$) alkyl group, which is unsubstituted or substituted one or more times with a fluorine atom or a group OALK, S(O)$_n$ALK or OS(O)$_n$ALK;

R$_9$ represents a group —OH, —CN, —CO$_2$H, NR$_{13}$R$_{14}$, —CONR$_{13}$R$_{14}$, —CONHNH$_2$, —CONHOH, —CONHSO$_2$Alk, —S(O)$_n$Alk, —SO$_2$CF$_3$, —SO$_2$NR$_{13}$R$_{14}$, —NHSO$_2$Alk, —NHSO$_2$CF$_3$, —NHSO$_2$NR$_{13}$R$_{14}$, or a radical chosen from:

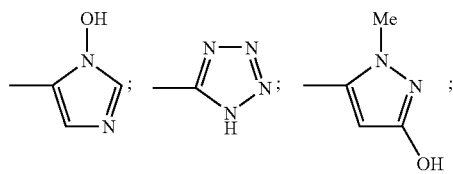

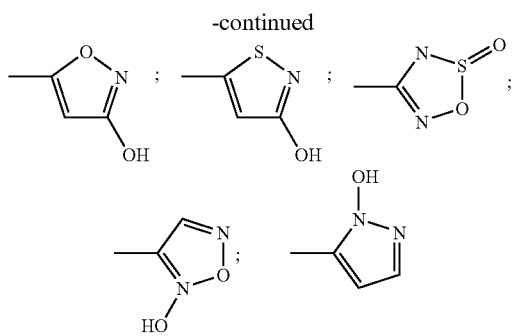

n represents 0, 1 or 2;

ALK represents a (C$_1$-C$_4$)alkyl group, which is unsubstituted or substituted with one or more fluorine atoms;

Alk represents a (C$_f$—C$_4$)alkyl group.

More particularly, a subject of the present invention is the compounds of formula:

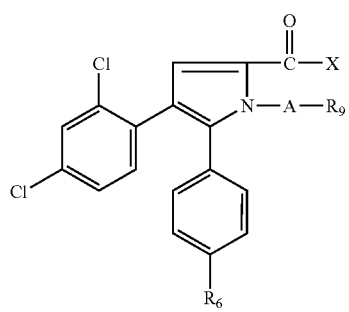

(II bis)

in which:

X represents a halogen atom or a hydroxyl, (C$_1$-C$_4$)alkoxy or benzyloxy group;

R$_6$ represents a chlorine or bromine atom;

A represents a group (CH$_2$)$_2$, (CH$_2$)$_3$, (CH$_2$)$_4$ or (CH$_2$)$_5$;

R$_9$ represents a group —CN, —COM, —SO$_2$CH$_3$, —NHSO$_2$CH$_3$ or —NHSO$_2$CF$_3$.

The examples that follow describe the preparation of certain compounds in accordance with the invention. These examples are not limiting and serve merely to illustrate the present invention. The numbers of the compounds given as examples refer to those given in the table below, which illustrate the chemical structures and the physical properties of a number of compounds according to the invention.

In the examples, the following abbreviations are used:

EtOAc: ethyl acetate
DCM: dichloromethane
DIPEA: diisopropylethylamine
DMF: N,N-dimethylformamide
m.p.: melting point
HBTU: N-[1-N-(dimethylamino)-1,2,3-triazolo[4,5-b]pyrid-1-ylmethylene]-N-methylmethanaminium hexafluorophosphate N-oxide
HOBt: 1-hydroxybenzotriazole
MeOH: methanol
PyBOP: benzotriazol-1-yloxytris(pyrrolidino)phosphonium hexafluorophosphate
RT: room temperature
TBTU: 2-(1H-benzotriazol-1-yl)-1,1,3,3-tetramethyluronium tetrafluoroborate
THF: tetrahydrofuran.

The nuclear magnetic resonance spectra are recorded at 200 MHz in DMSO-$d_6$. For the interpretation of the spectra, the following abbreviations are used:

s: singlet, d: doublet, t: triplet, m: unresolved complex, mt: multiplet, bs: broad singlet, dd: doubled doublet.

The compounds according to the invention are analyzed by LC/UV/MS coupling (liquid chromatography/UV detection/mass spectrometry). The molecular peak (MH$^+$) and the retention time (Rt) in minutes (min) are measured.

Conditions A

A Symmetry C18 2.1×50 mm, 3.5 μm column is used, at 30° C., flow rate 0.4 mL/minute.

The eluent is composed as follows:
solvent A: 0.005% trifluoroacetic acid (TFA) in water at pH 3.15;
solvent B: 0.005% TFA in acetonitrile.

Gradient:

| Time (minutes) | % A | % B |
|---|---|---|
| 0 | 100 | 0 |
| 10 | 10 | 90 |
| 15 | 10 | 90 |
| 16 | 100 | 0 |
| 20 | 100 | 0 |

Column temperature: 30° C., flow rate 0.4 ml/minute.

The UV detection is performed at λ=210 nm and the mass detection in positive ESI chemical ionization mode.

The UV detection is performed via a diode array detector between 210 and 400 nm and the mass detection in positive ESI mode.

PREPARATIONS

Preparation 1

A) Methyl 2-(((4-methylphenyl)sulfonyl)amino) pent-3-ynoate 2.5 g of 2-amino-3-butynoic acid are suspended in 45 ml of methanol at 0° C. 1.8 ml of thionyl chloride are added dropwise at this temperature and the mixture is then refluxed for 3 hours. The solution is concentrated and the residue is dried under reduced pressure. The resulting material is dissolved in 60 ml of acetonitrile followed by 5.4 ml of triethylamine, and 4.6 g of tosyl chloride are then added. The mixture is stirred at room temperature for 19 hours and then at 50° C. for a further one hour. After concentrating, the crude material is dissolved in dichloromethane and the organic phase is successively washed with saturated aqueous KHSO$_4$ solution and then with K$_2$CO$_3$. The organic phase is dried over magnesium sulfate and then filtered and finally concentrated to give 5.18 g of the expected compound.

$^1$H NMR: δ (ppm): 2.35: s: 3H, 2.45: m: 2H, 3.45: s: 3H, 3.9: dd: 1H, 7.35: d: 2H, 7.65: d: 2H, 8.4: d: 1H.

B) Methyl 5-(4-chlorophenyl)-2-(4-tosylsulfonylamino)pent-4-ynoate 1 g of the compound from the preceding step and 0.57 g of 4-chloroiodobenzene are dissolved in 20 ml of anhydrous DMF. The solution is degassed under vacuum for 30 minutes. 0.64 ml of triethylamine is then added, followed by addition of 0.28 g of tetrakis(triphenylphosphine)palladium(0) and 0.1 g of copper iodide. The mixture is stirred at room temperature under an argon atmosphere for 19 hours. The crude reaction material is concentrated and purified by chromatography on silica gel with cyclohexane/ethyl acetate (80/20; v/v). 1 g of the compound is recovered.

$^1$H NMR: δ (ppm): 2.35: s: 3H, 2.70-2.80: m: 2H, 3.45: s: 3H, 4.05: dd: 1H, 7.35: m: 4H, 7.4: d: 2H, 7.65: d: 2H, 8.51: d: 1H.

C) Methyl 5-(4-chlorophenyl)-4-iodo-1-(4-tosylsulfonyl)-2,3-dihydro-1H-pyrrole-2-carboxylate 1 g of the compound obtained in the preceding step is dissolved in 5 ml of anhydrous acetonitrile in the presence of 1 g of potassium carbonate at 0° C. 2 g of solid iodine are added in several small fractions with stirring at this temperature. The mixture is allowed to return to room temperature over 24 hours. The reaction is stopped with sodium thiosulfate solution until decolorized, and the organic phase is extracted with dichloromethane. After drying over magnesium sulfate, filtering and concentrating, 1.27 g of the expected compound are obtained.

LC/MS (conditions A): M=517, Rt=10.8 minutes.

D) Methyl 5-(4-chlorophenyl)-4-(2,4-dichlorophenyl)-1-tosylsulfonyl-2,3-dihydro-1H-pyrrole-2-carboxylate 15 g of the compound obtained in the preceding step and 6.8 g of 2,4-dichlorophenylboronic acid are dissolved in a mixture of 150 ml of methanol and 710 ml of toluene in the presence of 48 ml of sodium carbonate solution (2N). The reaction medium is left under argon for 30 minutes and 4.7 g of tetrakis(triphenylphosphine)palladium(0) are then added. The solution is heated at 60° C. for 4 hours under an inert atmosphere. After cooling, the crude product is concentrated and purified by chromatography on silica gel in toluene. 9.7 g of the expected compound are obtained in the form of a white powder.

$^1$H NMR: δ (ppm): 2.4: s: 3H, 2.75-2.95: m: 1H, 3.8: s: 3H, 5.15: d: 1H, 6.7: d: 1H, 7.1-7.7: m: 6H.

E) Methyl 5-(4-chlorophenyl)-4-(2,4-dichlorophenyl)-1H-pyrrole-2-carboxylate 9.7 g of the compound obtained in the preceding step are dissolved in 60 ml of anhydrous N,N-dimethylformamide. 5.4 ml of DBU (1,8-diaza-bicyclo[5.4.0]-undecene) are then added and the mixture is heated at 100° C. for 24 hours. The crude product is concentrated and, after addition of ethanol, a white precipitate appears. This precipitate is filtered off, and 6 g of the expected compound are collected.

$^1$H NMR: δ (ppm): 3.8: s: 3H, 6.9: s: 1H, 7.2: s: 1H, 7.25: s: 2H, 7.3-7.4: 3H, 7.65: dd: 1H, 12.4: s: 1H.

F) Methyl (4-chlorophenyl)-1-(2-cyanoethyl)-4-(2,4-dichlorophenyl)-1H-pyrrole-2-carboxylate 2.5 g of the compound obtained in the preceding step are dissolved in 24 ml of dioxane in the presence of 0.5 ml (0.53 g) of Triton B. The mixture is stirred for 1 hour at RT, 2 ml of acrylonitrile are then added and the mixture is refluxed for 3 days. The crude product is concentrated to dryness and then chromatographed on silica gel. 1.4 g of the expected compound are obtained.

LC/MS: M=432; Rt=12.02 minutes.

G) Methyl 1-(3-aminopropyl)-5-(4-chlorophenyl)-4-(2,4-dichlorophenyl)-1H-pyrrole-2-carboxylate 1 g of the compound obtained in the preceding step is dissolved in 20 ml of methanol, 1.06 g of $CoCl_2(H_2O)_6$ are added and the mixture is stirred at RT for 5 minutes. Next, 0.43 g of $NaBH_4$ are added portionwise and the mixture is stirred for 1 hour at RT. The medium is acidified with 4 ml of HCl (0.5 N). The compound is extracted with EtOAc to give, after drying over $MgSO_4$, filtering and concentrating, 1 g of the expected compound in the form of a white foam.
LC/MS: M=437; Rt=8.13 minutes.

H) Methyl 5-(4-chlorophenyl)-4-(2,4-dichlorophenyl)-1-(3-methanesulfonylaminopropyl)-1H-pyrrole-2-carboxylate 1 g of the amine obtained in the preceding step is dissolved in 20 ml of DCM in the presence of 0.61 ml (0.45 g) of triethylamine, followed by addition at RT of 0.17 ml of methylsulfonyl chloride, and the mixture is stirred for 48 hours. The crude reaction product is brought to dryness and then purified by chromatography on silica gel. 0.54 g of a white foam corresponding to the expected compound is obtained.
LC/MS: M=515; Rt=11.60 minutes.

I) 5-(4-Chlorophenyl)-4-(2,4-dichlorophenyl)-1-(3-methanesulfonyl-aminopropyl)-1H-pyrrole-2-carboxylic acid 0.63 g of the ester obtained in the preceding step is saponified in 10 ml of a THF/water mixture (9/1; v/v) in the presence of 5.4 ml of lithium hydroxide hydrate. The solution is refluxed for 19 hours and then brought to dryness. The crude product is acidified with aqueous HCl solution (10%) and the product is extracted with DCM. The organic phase is dried over $MgSO_4$ and then filtered and concentrated. 0.62 g of the expected product is obtained in the form of a white foam.
LC/MS: M=501; Rt=10.27 minutes.

Preparation 2

Ethyl 5-(4-chlorophenyl)-4-(2,4-dichlorophenyl)-1-(2-methanesulfonylethyl)-1H-pyrrole-2-carboxylate By working as described in preparation 1, steps A to E, ethyl 5-(4-chlorophenyl)-4-(2,4-dichlorophenyl)-1H-pyrrole-2-carboxylate is prepared.

0.8 g of this ester is dissolved in 20 ml of DMF and 0.32 g of NaH is then added at RT. The mixture is stirred for 30 minutes and 0.88 g of methyl vinyl sulfone is then added. The solution is refluxed for 19 hours. The medium is brought to dryness and the residue is purified by chromatography on silica gel. 0.2 g of a gum corresponding to the expected compound is collected.
LC/MS: M=499; Rt=11.87 minutes.

Preparation 3

A) 5-(4-Chlorophenyl)-4-(2,4-dichlorophenyl)-1H-pyrrole-2-carboxylic acid 7.8 g of the ester obtained in preparation 1, step E are dissolved in 100 ml of a THF/water mixture (90/10; v/v), 4.3 g of lithium hydroxide hydrate are then added and the mixture is refluxed for 19 hours. The mixture is brought to dryness and the solid residue is then washed several times with aqueous HCl (10%). The recovered solid is oven-dried to give 8.3 g of the expected compound (white solid).
LC/MS: M=365; Rt=10.57 minutes.

B) 1'-[5-(4-Chlorophenyl)-4-(2,4-dichlorophenyl)-1H-pyrrole-2-carbonyl]-[1,4']bipiperidyl-4'-carboxamide 2 g of the acid obtained above are dissolved in 40 ml of dichloromethane in the presence of 1.38 g (1.89 ml) of triethylamine, and 1.27 g of [1,4]bipiperidyl-4'-carboxamide are then added, followed by addition of 3.4 g of PyBOP. The mixture is stirred at RT for 24 hours. 2.3 g of a white precipitate corresponding to the expected compound are collected by filtration.
LC/MS: M=559; Rt=7.99 minutes.

Preparation 4

A) Ethyl 5-(4-chlorophenyl)-4-(2,4-dichlorophenyl)-1-(3-methanesulfanylpropyl)-1H-pyrrole-2-carboxylate By working as described in preparation 1, steps A to E, ethyl 5-(4-chlorophenyl)-4-(2,4-dichlorophenyl)-1H-pyrrole-2-carboxylate is prepared.

2 g of this ester are dissolved in 30 ml of anhydrous THF, and 2.2 g of 3-methylsulfanylpropan-1-ol are then added, followed by addition of 3.9 g of triphenylphosphine. At 0° C., 3.6 g of DEAD are added and the mixture is stirred at RT for 19 hours. The medium is brought to dryness and the residue is then purified by chromatography on silica gel. 2.4 g of an oil corresponding to the expected compound are collected.
LC/MS: $MH^+$=482; Rt=13.54 minutes.

B) Ethyl 5-(4-chlorophenyl)-4-(2,4-dichlorophenyl)-1-(3-methanesulfonylpropyl)-1H-pyrrole-2-carboxylate 2.4 g of the ester obtained in the preceding step are dissolved in 70 ml of dichloromethane. At 0° C., 6 g of mCPBA are added portionwise and the mixture is then stirred at RT for 2 hours. The medium is basified with aqueous NaOH solution (10%) and the product is extracted with DCM. The organic phase is dried over $MgSO_4$ and then filtered and concentrated. The residue is purified by chromatography on silica gel. 1.6 g of a yellowish foam corresponding to the expected product are collected.

C) 5-(4-Chlorophenyl)-4-(2,4-dichlorophenyl)-1-(3-methanesulfonylpropyl)-1H-pyrrole-2-carboxylic acid 1.6 g of the ester obtained in the preceding step B) are dissolved in 24 ml of MeOH. 1.7 g of KOH are added portionwise at RT until the potassium hydroxide pellets have totally dissolved, followed by addition of 4 ml of $H_2O$. The mixture is refluxed for 3 hours. Once cooled, the medium is acidified with aqueous 10% HCl solution and the product is extracted with DCM. The organic phase is dried over $MgSO_4$ and then filtered and concentrated. 1.5 g of a pale yellow foam corresponding to the expected product are obtained.

LC/MS: MH+=486; Rt=10.27 minutes.

Preparation 5

A) 1'-Benzyl-4,4-difluoro[1,4']bipiperidyl-4'-carboxamide 1.2 g of 1'-benzyl-4,4-difluoro[1,4']bipiperidyl-4'-carbonitrile, synthesized according to the method described in J. Med. Chem., 7, 1964, 619-622 from 1-benzylpiperid-4-one and commercial 4,4-difluoropiperidine, are suspended in 15 ml of concentrated sulfuric acid.

The medium is maintained at 60° C. for 3 hours. The crude product is cooled to 0° C. and then basified with aqueous NH$_4$OH solution. The aqueous phase is extracted with chloroform and the organic phase is dried over MgSO$_4$, filtered and then concentrated. 0.8 g of a white solid, purified by chromatography on silica gel, is obtained.

LC/MS: MH+=338; Rt=6.59 minutes.

B) 4,4-Difluoro[1,4']bipiperidyl-4'-carboxamide 3.3 g of the benzyl compound obtained above in preparation 5, step A) are dissolved in 30 ml of dichloromethane and, after cooling to 0° C., 1.57 g (1.19 ml) of chloroethyl chloroformate are then added. The temperature is then allowed to return to RT and the mixture is stirred for 3 hours. After evaporating off the solvents under vacuum, the residue obtained is dissolved in methanol and the mixture is refluxed for 1 hour and then re-evaporated to dryness. 3.3 g of a solid corresponding to the expected product are obtained.

Example 1

Compound 1

A) Ethyl 6-[5-(4'-carbamoyl[1,4']bipiperidyl-1'-carbonyl)-2-(4-chlorophenyl)-3-(2,4-dichlorophenyl)pyrrol-1-yl]hexanoate 0.9 g of the compound obtained in preparation 3, step B is dissolved in a mixture of 8 ml of acetone and 3 ml of DMF. 0.66 g of potassium carbonate is added, followed by addition of 0.32 ml of ethyl 6-bromohexanoate. The mixture is refluxed for 19 hours. The crude product is filtered and the filtrate is concentrated. 1.7 g of a white solid corresponding to the expected product are obtained, and are used without further purification in the saponification step.

LC/MS: M=702; Rt=8.90 minutes.

B) 6-[5-(4'-Carbamoyl[1,4']bipiperidyl-1'-carbonyl)-2-(4-chlorophenyl)-3-(2,4-dichlorophenyl)pyrrol-1-yl]hexanoic acid 1.1 g of the preceding ester are saponified in the presence of 0.66 g of lithium hydroxide hydrate in 10 ml of a THF/water mixture (9/1; v/v). After refluxing for 24 hours, the mixture is brought to dryness and then acidified with HCl solution (10%). The product is extracted with EtOAc. After drying over MgSO$_4$, filtering and then concentrating the organic phase, a crude product is obtained, which is chromatographed on silica gel. 0.9 g of the expected product is obtained in the form of a white solid.

LC/MS: M=674; Rt=8.13 minutes.

Example 2

Compound 11

1'-[5-(4-Chlorophenyl)-4-(2,4-dichlorophenyl)-1-(3-methanesulfonylpropyl)-1H-pyrrole-2-carbonyl]-4,4-dimethyl[1,4']bipiperidyl-4'-carboxamide 0.5 g of the acid obtained in step C) of preparation 4 is dissolved in 15 ml of DMF in the presence of 0.39 g (0.54 ml) of DIPEA, and 0.37 g of 4,4-dimethyl[1,4']bipiperidyl-4'-carboxamide is added, followed by addition of 0.58 g of HBTU and 0.07 g of HOBt. The mixture is stirred for 24 hours at RT. Once concentrated, the crude product is chromatographed on silica gel. 0.39 g of a solid crystallized from isopropyl ether, corresponding to the expected product, is obtained.

LC/MS: MH+=707; Rt=8 minutes.

Example 3

Compound 10

1'-[5-(4-Chlorophenyl)-4-(2,4-dichlorophenyl)-1-(3-methanesulfonylpropyl)-1H-pyrrole-2-carbonyl]-4,4-difluoro[1,4']bipiperidyl-4'-carboxamide 0.4 g of the acid obtained in step C) of preparation 4 is dissolved in 15 ml of DMF in the presence of 0.31 g (0.42 ml) of DIPEA, and 0.29 g of 4,4-difluoro[1,4']bipiperidyl-4'-carboxamide is added, followed by addition of 0.58 g of HBTU and 0.05 g of HOBt. The mixture is stirred for 19 hours at RT. Once concentrated, the crude product is chromatographed on silica gel. 0.3 g of a solid corresponding to the expected product is obtained.

LC/MS: MH+=730; Rt=10.36 minutes.

The tables that follow illustrate the chemical structures and the physical properties of a number of compounds according to the invention.

In this table, Me means methyl.

TABLE 1

(I)

[Structure: pyrrole core with C(O)-NR₁R₂ at one position, N-A-R₉ on nitrogen, a 2-chloro-4-R₃-phenyl group, and a 4-R₆-phenyl group]

| Compounds (Salt) | A-R₉ | R₆ | R₃ | —NR₁R₂ | Characterization m.p. °C. LC/MS |
|---|---|---|---|---|---|
| 1 | —(CH₂)₅—CO₂H | Cl | Cl | 4-(1-piperidinyl)-1-methylpiperidine-4-carboxamide | MH+ = 675<br>Rt = 8.13<br>102° C. |
| 2 | —(CH₂)₂—CO₂H | Cl | Cl | 4-(1-piperidinyl)-1-methylpiperidine-4-carboxamide | MH+ = 631<br>Rt = 7.54<br>137° C. |
| 3<br>CF₃CO₂H | —(CH₂)₂—CN | Cl | Cl | 4-(1-piperidinyl)-1-methylpiperidine-4-carboxamide | 125° C. |
| 4 | —(CH₂)₂—SO₂Me | Cl | Cl | 4-(1-piperidinyl)-1-methylpiperidine-4-carboxamide | MH+ = 655<br>Rt = 7.65 |
| 5 | —(CH₂)₂—SO₂Me | Br | Cl | 4-phenyl-1-methylpiperidine-4-carboxamide | MH+ = 702<br>Rt = 10.80 |
| 6 | —(CH₂)₂—SO₂Me | Br | Cl | 1-methyl-4-(1,3-benzodioxol-5-ylmethyl)piperazine | 135° C. |

TABLE 1-continued
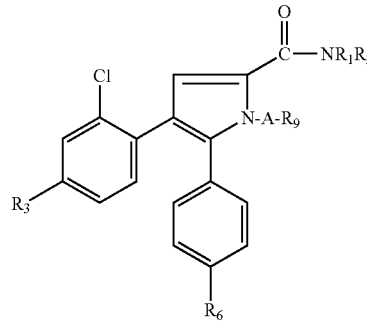
(I)
| Compounds (Salt) | A-R$_9$ | R$_6$ | R$_3$ | —NR$_1$R$_2$ | Characterization m.p. ° C. LC/MS |
|---|---|---|---|---|---|
| 7 | —(CH$_2$)$_2$—SO$_2$Me | Br | Cl | 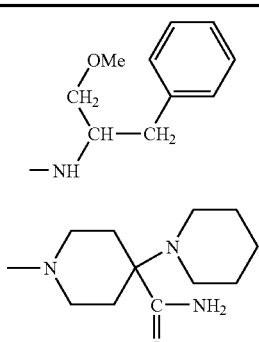 | MH+ = 665 Rt = 11.76 |
| 8 | —(CH$_2$)$_3$—NHSO$_2$Me | Cl | Cl | 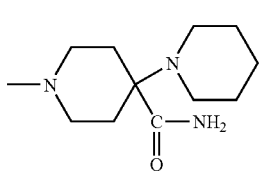 | 110° C. |
| 9 (HCl) | —(CH$_2$)$_3$—NHSO$_2$CF$_3$ | Cl | Cl | 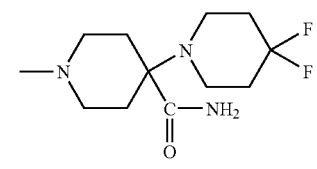 | 231° C. |
| 10 | —(CH$_2$)$_3$—NHSO$_2$Me | Cl | Cl | 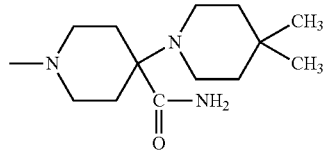 | MH+ = 730 Rt = 10.36 |
| 11 | —(CH$_2$)$_3$—SO$_2$Me | Cl | Cl | 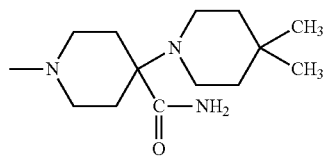 | MH+ = 707 Rt = 8 |
| 12 | —(CH$_2$)$_3$—NHSO$_2$Me | Cl | Cl | | MH+ = 722 Rt = 8.06 |
| 13 | —(CH$_2$)$_3$—SO$_2$Me | Cl | Cl | 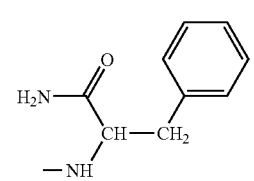 | MH+ = 632 Rt = 10.33 |

TABLE 1-continued (I)

| Compounds (Salt) | A-R₉ | R₆ | R₃ | —NR₁R₂ | Characterization m.p. ° C. LC/MS |
|---|---|---|---|---|---|
| 14 | —(CH₂)₂—SO₂Me | SMe | Cl | 4-methylpiperidinyl-(4,4-dimethylpiperidinyl)-carboxamide | MH+ = 705 Rt = 7.93 |
| 15 | —(CH₂)₃—NHSO₂Me | Cl | Cl | 4-methylpiperazinyl-CH₂-benzo[1,3]dioxole | MH+ = 702 Rt = 8.07 |
| 16 | —(CH₂)₃—NHSO₂Me | OMe | Cl | 4-methylpiperidinyl-(4,4-difluoropiperidinyl)-carboxamide | MH+ = 726 Rt = 9.88 |
| 17 | —(CH₂)₃—NHSO₂Me | OMe | H | 4-methylpiperidinyl-(4,4-difluoropiperidinyl)-carboxamide | MH+ = 692 Rt = 9.2 |
| 18 | —(CH₂)₃—NHSO₂Me | Cl | H | 4-methylpiperidinyl-(4,4-difluoropiperidinyl)-carboxamide | MH+ = 696 Rt = 15.16 |
| 19 | —(CH₂)₃—SO₂Me | Cl | Cl | (S)-2-(methylamino)-4-methylpentan-1-ol | MH+ = 585 Rt = 10.77 |

TABLE 1-continued
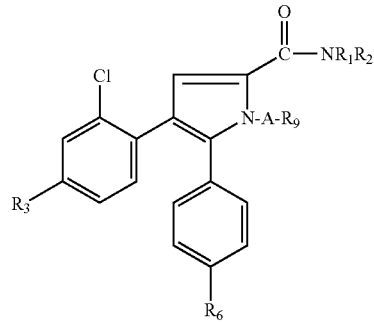
(I)
| Compounds (Salt) | A-R$_9$ | R$_6$ | R$_3$ | —NR$_1$R$_2$ | Characterization m.p. ° C. LC/MS |
|---|---|---|---|---|---|
| 20 | —(CH$_2$)$_3$—NHSO$_2$Me | OMe | Cl | 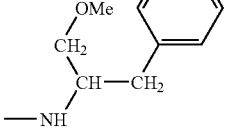 | MH+ = 696 Rt = 11 |
| 21 | —(CH$_2$)$_3$—NHSO$_2$Me | OMe | Cl | 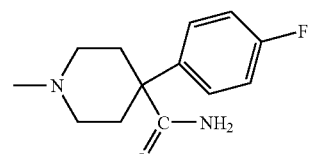 | MH+ = 701 Rt = 10.08 |
| 22 | —(CH$_2$)$_3$—NHSO$_2$Me | Cl | Cl | 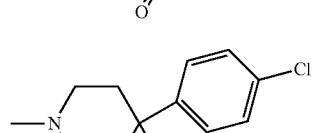 | MH+ = 721 Rt = 10.96 |
| 23 | —(CH$_2$)$_3$—NHSO$_2$Me | Cl | Cl | 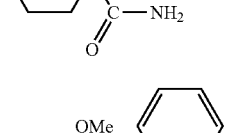 | MH+ = 648 Rt = 11.47 |
| 24 | —(CH$_2$)$_3$—NHSO$_2$Me | Cl | Cl | 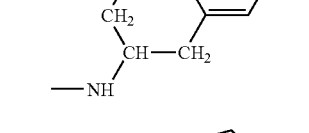 | MH+ = 705 Rt = 10.61 |
| 25 | —(CH$_2$)$_3$—NHSO$_2$Me | F | Cl | 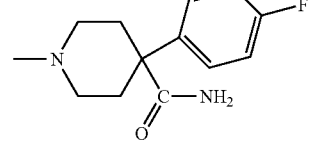 | MH+ = 714 Rt = 9.89 |
| 26 | —(CH$_2$)$_3$—NHSO$_2$Me | F | Cl | 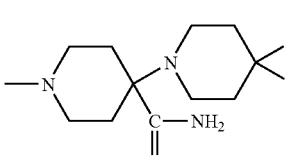 | MH+ = 645 Rt = 8.55 |

TABLE 1-continued (I)

[Structure: pyrrole core with C(=O)-NR₁R₂ group, N-A-R₉ substituent, 2-Cl-4-R₃-phenyl group, and 4-R₆-phenyl group]

| Compounds (Salt) | A-R₉ | R₆ | R₃ | —NR₁R₂ | Characterization m.p. ° C. LC/MS |
|---|---|---|---|---|---|
| 27 | —(CH₂)₃—NHSO₂Me | F | Cl | [1-methyl-4-(4-fluorophenyl)piperidin-4-yl]-C(=O)—NH₂ | MH+ = 689 Rt = 10.08 |
| 28 | —(CH₂)₃—NHSO₂Me | Cl | Cl | (2S)-2-(methylamino)-4-methylpentan-1-ol derivative (H₃C, H₃C, —NH, OH) | MH+ = 600 Rt = 10.82 |

The compounds of formula (I) show very good in vitro affinity ($IC_{50} \leq 5 \times 10^7 M$) for the $CB_1$ cannabinoid receptors, under the experimental conditions described by M. Rinaldi-Cannona et al. (FEBS Letters, 1994, 350, 240-244).

The antagonist nature of the compounds of formula (I) was demonstrated by means of the results obtained in models of inhibition of adenylate cyclase as described in M. Bouaboula et al., J. Biol. Chem., 1995, 270, 13973-13980, M. Rinaldi-Carmona et al., J. Pharmacol. Exp. Ther., 1996, 278, 871-878 and M. Bouaboula et al., J. Biol. Chem., 1997, 272, 22330-22339.

The interaction of a compound according to the invention with the $CB_1$ receptors present in the brain is determined in mice by means of the test of ex vivo binding of [3H]-CP55940 after intravenous injection or oral administration as described in M. Rinaldi-Cannona et al., FEBS Letters, 1994, 350, 240-244 and M. Rinaldi-Carmona et al., Life Sciences, 1995, 56, 1941-1947, M. Rinaldi-Carmona et al., J. Pharmacol. Exp. Ther., 2004, 310, 905-914 and Rinaldi-Carmona M. et al., JPET 2004, 310, 905-914.

The interaction of a compound according to the invention with the $CB_1$ receptors present peripherally is determined in mice by means of the test of reversion of the inhibitory effect of CP55940 on gastrointestinal transit after oral administration, as described in M. Rinaldi-Cannona et al., J. Pharmacol. Exp. Ther., 2004, 310, 905-914.

The toxicity of the compounds of formula (I) is compatible with their use as medicaments.

Thus, according to another of its aspects, a subject of the invention is medicaments for human or veterinary medicine, which comprise a compound of formula (I) or an addition salt thereof with a pharmaceutically acceptable acid, or alternatively a solvate or a hydrate of the compound of formula (I).

Thus, the compounds according to the invention may be used in man or animals (especially mammals including, in a non-limiting manner, dogs, cats, horses, cattle and sheep), in the treatment or prevention of diseases involving the $CB_1$ cannabinoid receptors.

For example, and in a non-limiting manner, the compounds of formula (I) are useful as psychotropic medicaments, especially for treating psychiatric disorders including anxiety, depression, mood disorders, insomnia, delirium disorders, obsessive disorders, psychoses in general, schizophrenia, attention deficit and hyperactivity (ADH) disorders in hyperactive children, and also for treating disorders associated with the use of psychotropic substances, especially in the case of substance abuse and/or substance dependency, including alcohol dependency and nicotine dependency.

The compounds of formula (I) according to the invention may be used as medicaments for treating migraine, stress, diseases of psychosomatic origin, panic attacks, epilepsy, movement disorders, in particular dyskinesia or Parkinson's disease, trembling and dystonia.

The compounds of formula (I) according to the invention may also be used as medicaments in the treatment of memory disorders, cognitive disorders, in particular in the treatment of senile dementia and Alzheimer's disease, and also in the treatment of attention or alertness disorders.

Furthermore, the compounds of formula (I) may be useful as neuroprotective agents, in the treatment of ischemia, cranial trauma and the treatment of acute or chronic neurodegenerative diseases: including chorea, Huntington's chorea and Tourette's syndrome.

The compounds of formula (I) according to the invention may be used as medicaments in the treatment of pain: neuropathic pain, acute peripheral pain, chronic pain of inflammatory origin, pain induced by an anticancer treatment.

The compounds of formula (I) according to the invention may be used as medicaments in human or veterinary medicine in the prevention and treatment of appetite disorders, appetence disorders (for sugars, carbohydrates, drugs, alcohol or any appetizing substance) and/or eating behavior, especially for the treatment of obesity or bulimia, and also for the treatment of type II diabetes or non-insulin-dependent diabetes and for the treatment of dyslipidemia and metabolic syndrome. Thus, the compounds of formula (I) according to the invention are useful in the treatment of obesity and of the risks associated with obesity, especially the cardiovascular risks.

Furthermore, the compounds of formula (I) according to the invention may be used as medicaments in the treatment and prevention of gastrointestinal disorders, diarrheic disorders, ulcers, vomiting, vesical and urinary disorders, liver diseases such as chronic cirrhosis, fibrosis, hepatic steatosis and steatohepatitis; and also disorders of endocrine origin, cardiovascular disorders, hypotension, atherosclerosis, hemorrhagic shock, septic shock, asthma, chronic bronchitis, chronic obstructive pulmonary diseases, Raynaud's syndrome, glaucoma, fertility disorders, premature labor, interruption of pregnancy, inflammatory phenomena, immune system diseases, in particular autoimmune and neuroinflammatory diseases such as rheumatoid arthritis, rectional arthritis, diseases resulting in demyelinization, multiple sclerosis, infectious and viral diseases such as encephalitis, strokes, and also as medicaments for anticancer chemotherapy, for the treatment of Guillain-Barré syndrome and for the treatment of bone diseases and osteoporosis. Furthermore, the compounds of formula (I) according to the invention may be used for their protective effects against drug-induced cardiotoxicity.

According to the present invention, the compounds of formula (I) are most particularly useful for the preparation of medicaments that are useful for preventing and treating psychiatric disorders, in particular schizophrenia, attention and alertness disorders, attention deficit and hyperactivity (ADH) disorders in hyperactive children; for preventing and treating memory deficiencies and cognitive disorders; dependence on and weaning from a substance, in particular alcohol dependency, nicotine dependency, weaning from alcohol and weaning from tobacco; acute or chronic neurodegenerative diseases.

More particularly, the compounds of formula (I) according to the present invention are useful in the preparation of medicaments that are useful for treating and preventing appetite disorders, appetence disorders, metabolic disorders, obesity, type II diabetes, metabolic syndrome, dyslipidemia, the gastrointestinal disorders, inflammatory phenomena, immune system diseases, psychotic disorders, alcohol dependency and nicotine dependency.

According to one of its aspects, the present invention relates to the use of a compound of formula (I), pharmaceutically acceptable salts thereof and solvates or hydrates thereof, for treating the disorders and diseases indicated above.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt, a solvate or a hydrate of the said compound, and also at least one pharmaceutically acceptable excipient.

The said excipients are chosen, according to the pharmaceutical form and the desired mode of administration, from the usual excipients known to those skilled in the art.

The pharmaceutical compositions according to the present invention may contain, along with a compound of formula (I), one (or more) other active principle that is useful in the treatment of the disorders and diseases indicated above.

Thus, a subject of the present invention is also pharmaceutical compositions containing a compound of formula (I) according to the present invention combined with one (or more) active principle chosen from one of the following therapeutic classes:
  another antagonist or allosteric modulator of the cannabinoid $CB_1$ receptors;
  a cannabinoid $CB_2$ receptor modulator;
  an angiotensin II $AT_1$ receptor antagonist;
  a converting enzyme inhibitor;
  a calcium antagonist;
  a diuretic;
  a beta-blocker;
  an antihyperlipemiant or an antihypercholesterolemiant;
  an antidiabetic agent;
  another anti-obesity agent or agent acting on metabolic disorders;
  a nicotine agonist or a partial nicotine agonist;
  an antidepressant, an antipsychotic agent or an anxiolytic agent;
  an anticancer agent or an antiproliferative agent;
  an opioid antagonist;
  and also:
  an agent for improving the memory;
  an agent that is useful in the treatment of alcoholism or the symptoms of weaning;
  an agent that is useful for treating osteoporosis;
  a non-steroidal or steroidal anti-inflammatory drug;
  an anti-infectious agent;
  an analgesic;
  an antiasthmatic agent.

The term "angiotensin II $AT_1$ receptor antagonist" means a compound such as candesartan, cilexitil, eprosartan, irbesartan, losartan potassium, olmesartan medoxomil, telmisartan or valsartan, each of these compounds themselves possibly being combined with a diuretic such as hydrochlorothiazide.

The term "converting enzyme inhibitor" means a compound such as alacepril, benazepril, captopril, cilazapril, enalapril, enalaprilat, fosinopril, imidapril, lisinopril, moexipril, perindopril, quinapril, ramipril, spirapril, temocapril, trandolapril or zofenopril, each of these compounds itself possibly being combined with a diuretic such as hydrochlorothiazide or indapamide or with a calcium antagonist such as amlodipine, diltiazem, felodipine or verapamil.

The term "calcium antagonist" means a compound such as amlodipine, aranidipine, benidipine, bepridil, cilnidipine, diltiazem, efonidipine hydrochloride ethanol, fasudil, felodipine, isradipine, lacidipine, lercanidipine hydrochloride, manidipine, mibefradil hydrochloride, nicardipine, nifedipine, nilvadipine, nimodipine, nisoldipine, nitrendipine, terodiline or verapamil.

The term "beta-blocker" means a compound such as acebutolol, alprenolol, amosulalol, arotinolol, atenolol, befunolol, betaxolol, bevantolol, bisoprolol, bopindolol, bucumolol, bufetolol, bunitrolol, butofilolol, carazolol, carteolol, carvedilol, cloranolol, epanolol, esmolol, indenolol, labetalol, landiolol, levobunolol, levomoprolol, mepindolol, metipranolol, metoprolol, nadolol, nebivolol, nifenalol, nipradilol, oxprenolol, penbutolol, pindolol, propanolol, salmeterol, sotalol, talinolol, tertatolol, tilisolol, timolol, xamoterol or xibenolol.

The term "antihyperlipidemiant or antihypercholesterolemiant" means a compound chosen from fibrates such as alufibrate, beclobrate, bezafibrate, ciprofibrate, clinofibrate, clofibrate, etofibrate or fenofibrate; statins (HMG-CoA reductase inhibitors) such as atorvastatin, fluvastatin sodium, lovastatin, pravastatin, rosuvastatin or simvastatin, or a compound such as acipimox, aluminum nicotinate, azacosterol, cholestyramine, dextrothyroxine, meglutol, niceritrol, nicoclonate, nicotinic acid, beta-sitosterin or tiadenol.

The term "antidiabetic agent" means a compound belonging to one of the following classes: sulfonylureas, biguanidines, alpha-glucosidase inhibitors, thiazolidinediones, metiglinides such as acarbose, acetohexamide, carbutamide, chlorpropamide, glibenclamide, glibornuride, gliclazide, glimepiride, glipizide, gliquidone, glisoxepide, glybuzole, glymidine, metahexamide, metformin, miglitol, nateglinide, pioglitazone, repaglinide, rosiglitazone, tolazamide, tolbutamide, troglitazone or voglibose, and also insulin and insulin analogues.

The term "another anti-obesity agent or agent acting on metabolic disorders" means a compound such as amfepramone, benfluorex, benzphetamine, indanorex, mazindole, mefenorex, methamphetamine, D-norpseudoephedrine, sibutramine, a topiramate, a lipase inhibitor (orlistat or cetilistat), a PPAR agonist (peroxisome proliferator-activated receptor agonist), a dopamine agonist, a leptin receptor agonist, a serotonin reuptake inhibitor, a beta-3 agonist, a CCK-A agonist, an NPY inhibitor, an MC 4 (melanocortin 4) receptor agonist, an MCH (melanin concentrating hormone) receptor antagonist, an orexin antagonist, a phosphodiesterase inhibitor, an 11βHSD (11β-hydroxy steroid dehydrogenase) inhibitor, a DPP-IV (dipeptidyl peptidase IV) inhibitor, a histamine H3 antagonist (or inverse agonist), a CNTF (ciliary neurotrophic factor) derivative, a GHS (growth hormone secretagogue) receptor agonist, a ghrelin modulator, a diacylglycerol acyltransferase (DGAT) inhibitor, a phosphodiesterase (PDE) inhibitor, a thyroid hormone agonist, a glucocorticoid receptor antagonist, a stearoyl-CoA desaturase (SCD) inhibitor, a phosphate, glucose, fatty acid or dicarboxylate transporter modulator, a $5HT_2$ antagonist, a $5HT_6$ antagonist or a bombesin agonist.

The term "opioid antagonist" means a compound such as naltrexone, naloxone or nalmefene.

The term "agent useful in the treatment of alcoholism and weaning symptoms" means acamprosate, benzodiazepines, beta-blockers, clonidine and carbamazepine.

The term "agent useful for treating osteoporosis" means, for example, bisphosphonates such as etidronate, clodronate, tiludronate or risedronate.

According to the present invention, it is also possible to combine other compounds with antihyperlipemiant, antihypercholesterolemiant, antidiabetic or anti-obesity properties. More particularly, compounds belonging to one of the following classes may be combined:

PTP 1 B (protein tyrosine phosphase-1B) inhibitors, VPAC 2 receptor agonists, GLK modulators, retinoid modulators, glycogen phosphorylase (HGLPa) inhibitors, glucagon antagonists, glucose-6 phosphate inhibitors, pyruvate dehydrogenase kinase (PDK) activators, RXR, FXR or LXR modulators, SGLT (sodium-dependent glucose transporter) inhibitors, CETP (cholesteryl ester transfer protein) inhibitors, squalene synthetase inhibitors, squalene epoxidase inhibitors, triglyceride synthesis inhibitors, LDL (low-density lipoprotein) receptor inducers, IBAT inhibitors, FBPase (fructose-1,6-biphosphatase) inhibitors, CART (cocaine-amphetamine-regulated transcript) modulators, orexin receptor antagonists.

According to another aspect of the invention, the compound of formula (I), or a pharmaceutically acceptable salt thereof or a solvate thereof, and the other combined active principle may be administered simultaneously, separately or sequentially over time.

The term "simultaneous use" means the administration of the compounds of the composition according to the invention included in the same pharmaceutical form.

The term "separate use" means the administration, at the same time, of the two compounds of the composition according to the invention, each included in a separate pharmaceutical form.

The term "use sequentially over time" means the successive administration of the first compound of the composition according to the invention, included in one pharmaceutical form, and then of the second compound of the composition according to the invention, included in a separate pharmaceutical form. In this case, the time elapsed between the administration of the first compound of the composition according to the invention and the administration of the second compound of the same composition according to the invention generally does not exceed 24 hours.

In the pharmaceutical compositions of the present invention for oral, sublingual subcutaneous, intramuscular, intravenous, topical, local, intratracheal, intranasal, transdermal or rectal administration, the active principle of formula (I) above, or the possible salt, solvate or hydrate thereof, may be administered in a unit form of administration, as a mixture with standard pharmaceutical excipients, to man and animals for the prophylaxis or treatment of the above disorders or diseases.

The appropriate unit forms of administration include oral-route forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. For topical application, the compounds according to the invention may be used in creams, gels, pomades or lotions.

By way of example, a unit form of administration of a compound according to the invention in tablet form may comprise the following components:

| | |
|---|---:|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

Via the oral route, the dose of active principle administered per day may be from 0.01 to 100 mg/kg in one or more dosage intakes, preferentially 0.02 to 50 mg/kg.

There may be particular cases in which higher or lower dosages are appropriate; such dosages do not depart from the context of the invention. According to the usual practice, the dosage that is appropriate to each patient is determined by the doctor according to the mode of administration and the weight and response of the said patient.

According to another of its aspects, the present invention also relates to a method for treating the pathologies indicated above, which comprises the administration to a patient of an effective dose of a compound according to the invention, or a pharmaceutically acceptable salt or hydrate or solvate thereof.

What is claimed is:
1. A compound of the formula (I):

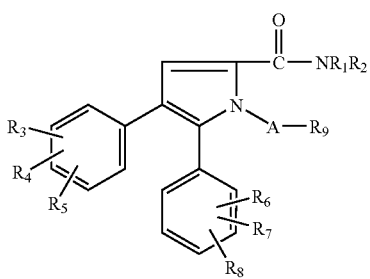

in which:

A represents:
  a $(C_1\text{-}C_6)$alkylene group, which is unsubstituted or substituted one or more times with a $(C_1\text{-}C_3)$alkyl group;
  a group

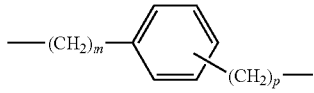

wherein m=0, 1 or 2 and p=0 or 1;

$R_1$ represents hydrogen or a $(C_1\text{-}C_4)$alkyl;

$R_2$ represents:
  a $(C_3\text{-}C_{10})$alkyl group, which is unsubstituted or substituted with a trifluoromethyl group; hydroxyl, $(C_1\text{-}C_4)$ alkoxy, a fluorine atom or a $CONH_2$ group;
  a non-aromatic $C_3\text{-}C_{12}$ carbocyclic radical, which is unsubstituted or substituted one or more times with a $(C_1\text{-}C_4)$alkyl, hydroxyl, cyano or $(C_1\text{-}C_4)$alkoxy group, a group $COR_{12}$ or a fluorine atom;
  an indanyl;
  a 1,2,3,4-tetrahydro-1- or -2-naphthyl;
  a monooxygen or monosulfur heterocyclic radical of 5 to 7 atoms, which is unsubstituted or substituted one or more times with a $(C_1\text{-}C_4)$alkyl group;
  a mononitrogen heterocyclic radical of 5 to 7 atoms, which is unsubstituted or substituted one or more times with a $(C_1\text{-}C_4)$alkyl group, the nitrogen atom moreover being substituted with a $(C_1\text{-}C_4)$alkyl, phenyl, benzyl, $(C_1\text{-}C_4)$alkoxycarbonyl or $(C_1\text{-}C_4)$alkanoyl group, the phenyl or benzyl groups being unsubstituted or substituted one or more times with a halogen atom or a $(C_1\text{-}C_4)$alkyl, trifluoromethyl, hydroxyl or $(C_1\text{-}C_4)$alkoxy group;
  a benzothiophenyl or an indolyl, the said radicals being unsubstituted or substituted one or more times with a $(C_1\text{-}C_4)$alkyl group;
  a $(C_1\text{-}C_3)$alkylene group bearing a non-aromatic $C_3\text{-}C_{10}$ carbocyclic radical, which is unsubstituted or substituted one or more times with a $(C_1\text{-}C_4)$alkyl, hydroxyl, $(C_1\text{-}C_4)$alkoxy or cyano group or a group $COR_{12}$;
  a $(C_1\text{-}C_3)$alkylene group bearing a monooxygen, monosulfur or mononitrogen heteroaromatic or non-heteroaromatic heterocyclic radical of 5 to 7 atoms, which is unsubstituted or substituted one or more times with a $(C_1\text{-}C_4)$alkyl group;
  a $(C_1\text{-}C_3)$alkylene group bearing an indolyl or benzothiophenyl radical, the said radical being unsubstituted or substituted one or more times with a $(C_1\text{-}C_4)$ alkyl group and the alkylene being unsubstituted or substituted with a hydroxyl, methyl or methoxy group or with a group $COR_{12}$;
  a $(C_1\text{-}C_3)$alkylene group bearing a $(C_1\text{-}C_4)$alkylthio group;
  a phenylalkylene group in which the alkylene is $(C_1\text{-}C_3)$, which is unsubstituted or substituted on the alkylene with one or more methyl, hydroxyl, hydroxymethyl, methoxy or methoxymethyl groups, or a group $COR_{12}$, and which is unsubstituted on the phenyl or substituted on the phenyl with one or more identical or different substituents chosen from a halogen atom and a $(C_1\text{-}C_4)$alkyl, trifluoromethyl, $(C_1\text{-}C_4)$alkoxy or trifluoromethoxy group;
  a benzhydryl or benzhydrylmethyl group;
  a group $NR_{10}R_{11}$;

or $R_1$ and $R_2$, together with the nitrogen atom to which they are attached, constitute:
  either a morpholinyl group
    or a piperazin-1-yl or 1,4-diazepan-1-yl radical, which is unsubstituted or substituted with a phenyl, benzyl, benzodioxolyl, benzodioxolylmethyl or tetrahydrofurylcarbonyl group or with a group $COR_{12}$ or $CH_2COR_{12}$, the benzyl group itself being unsubstituted or substituted with one or more halogen atoms or with one or more methoxy or methoxymethyl groups;
    or a piperid-1-yl, pyrrolidin-1-yl or azetidin-1-yl radical, which is unsubstituted or substituted one or two times with a substituent independently chosen from:
  a fluorine atom or a group $(C_1\text{-}C_4)$alkyl, hydroxyl, cyano, $COR_{12}$, $NR_{13}R_{14}$, $NHCOR_{15}$, $CH_2COR_{12}$, $SO_2Alk$; or $SO_2NR_{13}R_{14}$;
  a phenyl, benzyl or pyridyl group, the said phenyl, benzyl or pyridyl groups being unsubstituted or substituted one or more times with a substituent each independently chosen from a halogen atom, and a methyl, trifluoromethyl, hydroxyl, $(C_1\text{-}C_4)$alkoxy or cyano group;
  a piperid-1-yl, pyrrolidin-1-yl or azetidin-1-yl group, the said piperid-1-yl, pyrrolidin-1-yl or azetidin-1-yl groups being unsubstituted or substituted one or more times with a fluorine atom or a $(C_1\text{-}C_4)$alkyl, $(C_1\text{-}C_4)$alkoxy, hydroxyl, trifluoromethyl or $OCF_3$ group;

$R_3$, $R_4$, $R_5$, $R_6$, $R_7$ and $R_8$ represent, independently of each other, a hydrogen or halogen atom, a group CN, $S(O)_n$ ALK or $OS(O)_n$ALK, a group $(C_1\text{-}C_7)$alkyl, which is unsubstituted or substituted one or more times with a substituent each independently chosen from a fluorine atom, and group OALK, $S(O)_n$ALK, $OS(O)_n$ALK and $NHSO_2$Alk, or a group $(C_1\text{-}C_6)$alkoxy, which is unsubstituted or substituted with one or more substituents each independently chosen from a fluorine atom and a group OALK, $S(O)_n$ALK, $OS(O)_n$ALK and $NHSO_2$Alk;

$R_9$ represents a group —OH, —CN, —$CO_2$H, $NR_{13}R_{14}$, —$CONR_{13}R_{14}$, —$NR_1COR_{13}$, —$CONHNH_2$, —CONHOH, —$CONHSO_2$Alk, —$S(O)_n$Alk, —$SO_2CF_3$, —$SO_2NR_{13}R_{14}$, —$NR_1SO_2$Alk, —$NR_1SO_2CF_3$, —$NR_1SO_2NR_{13}R_{14}$, or a radical chosen from:

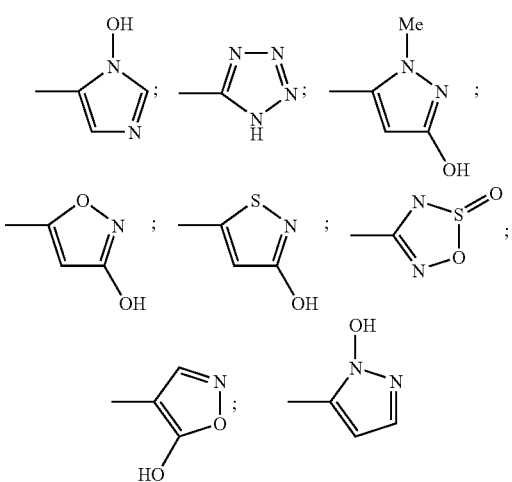

$R_{10}$ represents a hydrogen atom or a methyl group;

$R_{11}$ represents a $(C_3-C_6)$alkyl, phenyl or $(C_3-C_{10})$cycloalkyl group, the phenyl and cycloalkyl groups being unsubstituted or substituted with one or more substituents independently chosen from a halogen atom and a $(C_1-C_4)$alkyl or trifluoromethyl group;

or $R_{10}$ and $R_{11}$, together with the nitrogen atom to which they are attached, constitute a saturated or unsaturated, bridged or non-bridged heterocyclic radical of 4 to 11 atoms, possibly comprising a spirane carbon and possibly containing a second heteroatom chosen from O and N, the said radical being unsubstituted or substituted one or more times with a substituent each independently chosen from a hydroxyl, $(C_1-C_4)$alkyl or $(C_1-C_4)$ alkoxycarbonyl or $COR_{12}$ group, or a phenyl group that is unsubstituted or substituted with one or more substituents independently chosen from a halogen atom and a $(C_1-C_4)$alkyl group;

$R_{12}$ represents a $(C_1-C_4)$alkyl, phenyl, benzyl, $(C_1-C_4)$ alkoxy or trifluoromethyl group or a group $NR_{13}R_{14}$;

$R_{13}$ and $R_{14}$ each independently represent a hydrogen atom or a $(C_1-C_6)$alkyl group optionally substituted with one or more groups OH, F or OALK, or $R_{13}$ or $R_{14}$, together with the nitrogen atom to which they are attached, constitute a 4- to 7-membered heterocyclic radical possibly comprising a second heteroatom chosen from a nitrogen, oxygen or sulfur atom;

$R_{15}$ represents a $(C_1-C_4)$alkyl or trifluoromethyl group;

n represents 0, 1 or 2;

ALK represents a $(C_1-C_4)$alkyl group, which is unsubstituted or substituted with one or more fluorine atoms; and Alk represents a $(C_1-C_4)$alkyl group;

or a salt thereof.

2. The compound of formula (I) according to claim 1, wherein:

$R_1$ represents hydrogen and $R_2$ represents a group $NR_{10}R_{11}$ in which $R_{10}$ and $R_{11}$, together with the nitrogen atom to which they are attached, constitute a saturated heterocyclic radical of 5 to 11 carbon atoms, which is unsubstituted or substituted one or more times with a $(C_1-C_4)$ alkyl;

or $R_1$ and $R_2$, together with the nitrogen atom to which they are attached, constitute a piperid-1-yl radical gem-disubstituted with a phenyl, benzyl, pyrrolidin-1-yl, piperid-1-yl or 4,4-difluoropiperid-1-yl group, a cyano, $(C_1-C_3)$alkanoyl, aminocarbonyl, methanesulfonyl, N-methylsulfonyl or N,N-dimethylsulfonyl group;

or $R_1$ and $R_2$ together represent a piperazin-1-yl group in which 4-position is substituted with a benzodioxolyl or benzodioxolylmethyl group or with a benzyl, which is itself unsubstituted or substituted with one or more halogen atoms or with one or more methoxy or methoxymethyl groups;

$R_3$, $R_4$, $R_5$, $R_6$, $R_7$ and $R_8$ represent, independently of each other, a hydrogen or halogen atom or a methoxy group; and $A-R_9$ is as defined in claim 1;

or a salt thereof.

3. The compound of formula (I) according to claim 1, wherein:

$R_1$ represents hydrogen and $R_2$ represents a piperid-1-yl radical or a $(C_1-C_3)$alkylene radical substituted with a phenyl and with a methoxy or methoxycarbonyl group;

or $R_1$ represents hydrogen and $R_2$ represents a phenylalkylene group in which the alkylene is of $(C_1-C_3)$, unsubstituted on the alkylene or substituted on the alkylene with a methyl, hydroxyl, hydroxymethyl, methoxy or methoxymethyl group, and unsubstituted on the phenyl or substituted one or more times on the phenyl with a halogen atom or a methyl, trifluoromethyl, hydroxyl or methoxy group;

or $R_1$ and $R_2$, together with the nitrogen atom to which they are attached, represent a piperid-1-yl radical 4-gem-disubstituted with a phenyl or piperid-1-yl group and with an acetyl, aminocarbonyl or cyano group;

or $R_1$ and $R_2$ together represent a piperazin-1-yl group 4-substituted with a benzodioxolylmethyl or a benzyl, which is itself unsubstituted or substituted with a halogen atom;

$R_6$ is a 4-chloro or a 4-methoxy and $R_3$ and $R_4$ represent 2,4-dichloro or 2-chloro, $R_5$, $R_7$ and $R_8$ representing a hydrogen atom;

A represents a group $(CH_2)_q$ with q=2, 3, 4 or 5;

$R_9$ represents a group chosen from: —$CO_2H$, —$NHSO_2CF_3$, —$NHSO_2CH_3$, or —$SO_2CH_3$;

or a salt thereof.

4. The compound of formula (I) according to claim 1, wherein:

$NR_1R_2$ represents:

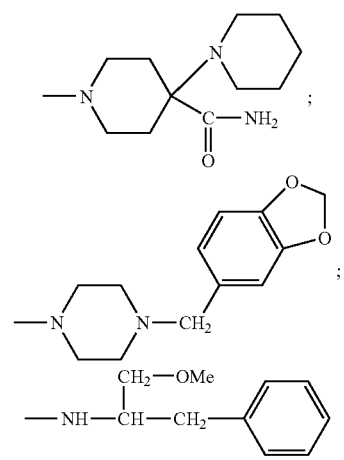

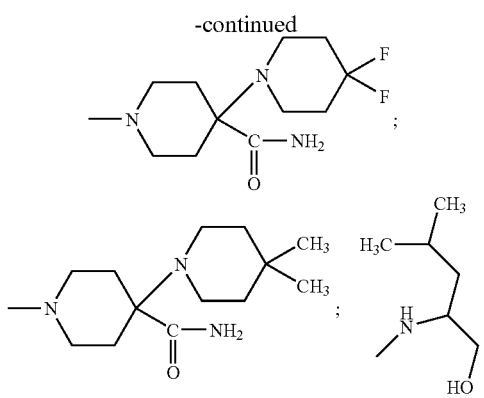

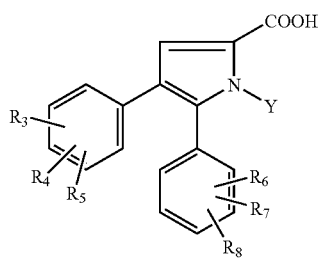

$R_3$, $R_4$ and $R_6$ each represent a halogen atom;
$R_5$, $R_7$ and $R_8$ each represent a hydrogen atom;
A represents a benzyl or a $(C_2-C_5)$alkylene group, which is unsubstituted or substituted one or more times with a methyl;
$R_9$ represents a group CN, $CO_2H$, $SO_2CH_3$, $NHSO_2CH_3$ or $NHSO_2CF_3$;
or a salt thereof.

5. A process for preparing a compound of formula (I) according to claim 1, comprising:
reacting the acid of formula (II):

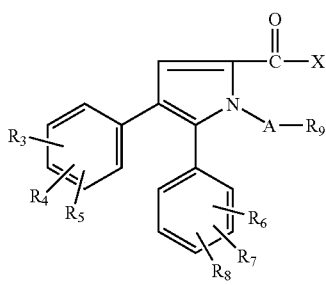

with an amine of formula $HNR_1R_2$ (III), wherein $R_1$, $R_2$, $R_3$, $R_4$, $R_5$, $R_6$, $R_7$ and $R_8$ are as defined in claim 1 and Y represents either a hydrogen atom or the group $A-R_9$, or a precursor of the group $A-R_9$, wherein $A-R_9$ is as defined in claim 1; and
converting, where appropriate, the substituent Y into a group $A-R_9$.

6. A compound of formula (II bis):

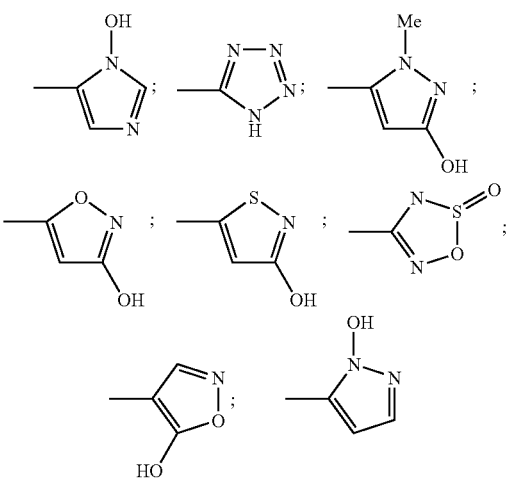

in which:
X represents a halogen atom or a hydroxyl, $(C_1-C_4)$alkoxy or benzyloxy group;

A represents:
a $(C_1-C_6)$ alkylene group, which is unsubstituted or substituted one or more times with a $(C_1-C_3)$alkyl group;
a group

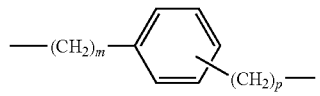

wherein m=0, 1 or 2 and p=0 or 1;
$R_3$, $R_4$, $R_5$, $R_6$, $R_7$ and $R_8$ represent, independently of each other, a hydrogen or halogen atom, a $(C_1-C_6)$alkoxy group, a group $S(O)_nALK$, $OS(O)_nALK$ or a $(C_1-C_7)$ alkyl group, which is unsubstituted or substituted one or more times with a fluorine atom or a group OALK, $S(O)_nALK$ or $OS(O)_nALK$;
$R_9$ represents a group —OH, —CN, —$CO_2H$, $NR_{13}R_{14}$, —$CONR_{13}R_{14}$, —$CONHNH_2$, —CONHOH, —$CONHSO_2Alk$, —$S(O)_nAlk$, —$SO_2CF_3$, —$SO_2NR_{13}R_{14}$, —$NHSO_2Alk$, —$NHSO_2CF_3$, —$NHSO_2NR_{13}R_{14}$, or a radical chosen from:

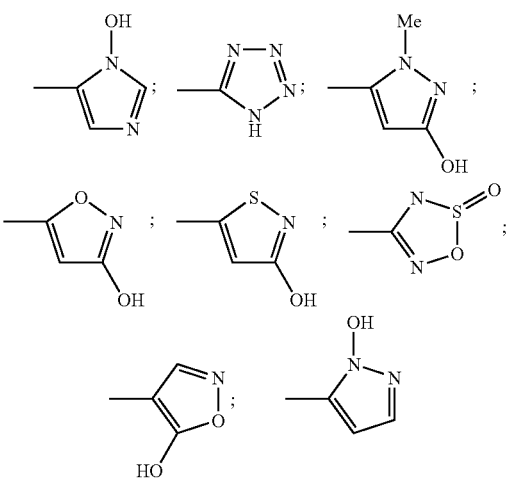

n represents 0, 1 or 2; and wherein
ALK represents a $(C_1-C_4)$alkyl group, which is unsubstituted or substituted with one or more fluorine atoms; and
Alk represents a $(C_1-C_4)$alkyl group.

7. A pharmaceutical composition comprising a compound of formula (I) according to claim 1 or a pharmaceutically acceptable salt thereof in combination with at least one pharmaceutically acceptable excipient.

8. A pharmaceutical composition comprising a compound of formula (I) according to claim 2 or a pharmaceutically acceptable salt thereof in combination with at least one pharmaceutically acceptable excipient.

9. A pharmaceutical composition comprising a compound of formula (I) according to claim 3 or a pharmaceutically acceptable salt thereof in combination with at least one pharmaceutically acceptable excipient.

10. A pharmaceutical composition comprising a compound of formula (I) according to claim 4 or a pharmaceutically acceptable salt thereof in combination with at least one pharmaceutically acceptable excipient.

* * * * *